US009693881B2

(12) United States Patent
Lorio et al.

(10) Patent No.: US 9,693,881 B2
(45) Date of Patent: Jul. 4, 2017

(54) KNEE SIZING AND BALANCING INSTRUMENT

(71) Applicant: Biomet Manufacturing, LLC, Warsaw, IN (US)

(72) Inventors: Jerry J. Lorio, Benton, AR (US); Brian A. Uthgenannt, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/732,861

(22) Filed: Jun. 8, 2015

(65) Prior Publication Data

US 2015/0335448 A1 Nov. 26, 2015

Related U.S. Application Data

(63) Continuation of application No. 13/555,304, filed on Jul. 23, 2012, now Pat. No. 9,050,197.

(51) Int. Cl.
*A61F 2/46* (2006.01)
*A61B 17/02* (2006.01)
(Continued)

(52) U.S. Cl.
CPC .......... *A61F 2/4657* (2013.01); *A61B 17/025* (2013.01); *A61B 17/1675* (2013.01);
(Continued)

(58) Field of Classification Search
CPC ............ A61F 2/4657; A61F 2002/4658; A61F 2002/4661; A61F 2002/4666;
(Continued)

(56) References Cited

U.S. PATENT DOCUMENTS 5,275,603 A * 1/1994 Ferrante ............... A61B 17/157
606/86 R
5,540,696 A * 7/1996 Booth, Jr. ............ A61B 17/025
606/102
(Continued)

OTHER PUBLICATIONS

"U.S. Appl. No. 13/555,304, Examiner Interview Summary mailed Jul. 24, 2014", 3 pgs.
(Continued)

*Primary Examiner* — Matthew Lawson
*Assistant Examiner* — Amy Sipp
(74) *Attorney, Agent, or Firm* — Schwegman Lundberg & Woessner, P.A.

(57) ABSTRACT

A method of sizing and balancing a knee including: placing an integrated orthopedic instrument in contact with a resected distal femoral surface of a femur of a knee in flexion such that medial and lateral posterior feet of a tensor frame of the instrument are in contact with posterior condyles of the femur and such that medial and lateral posterior feet of a sizer body of the instrument are positioned on a spacer placed on a resected proximal surface of the patient's tibia; securing first and second wings extending from a central portion of the tensor frame on the resected distal femoral surface; rotating the sizer body relative to the tensor frame via a rotation mechanism that connects the sizer body and the tensor frame to balance the ligaments; and sizing the patient's femur by moving a stylus coupled to the sizer body on an anterior surface of the femur.

16 Claims, 19 Drawing Sheets

(51) Int. Cl.
*A61B 17/16* (2006.01)
*A61F 2/38* (2006.01)
*A61B 17/15* (2006.01)
*A61B 90/00* (2016.01)

(52) U.S. Cl.
CPC .............. *A61F 2/38* (2013.01); *A61B 17/154* (2013.01); *A61B 2017/0268* (2013.01); *A61B 2090/067* (2016.02); *A61F 2/3859* (2013.01); *A61F 2002/3895* (2013.01); *A61F 2002/4658* (2013.01); *A61F 2002/4668* (2013.01)

(58) Field of Classification Search
CPC ........... A61F 2002/4668; A61B 17/025; A61B 17/1675; A61B 17/154; A61B 2017/0268; A61B 2090/067
USPC .............................. 606/102, 87–89, 90, 86 R
See application file for complete search history.

(56) References Cited

U.S. PATENT DOCUMENTS

| | | | |
|---|---|---|---|
| 5,597,379 A * | 1/1997 | Haines | A61B 17/1764 606/80 |
| 5,681,316 A * | 10/1997 | DeOrio | A61B 17/157 606/87 |
| 5,776,137 A * | 7/1998 | Katz | A61B 17/155 606/102 |
| 5,860,980 A | 1/1999 | Axelson, Jr. et al. | |
| 5,911,723 A | 6/1999 | Ashby et al. | |
| 6,056,756 A | 5/2000 | Eng et al. | |
| 6,588,243 B1 | 7/2003 | Hyatt, Jr. et al. | |
| 6,705,809 B2 | 3/2004 | Manos, Jr. | |
| 7,261,719 B1 * | 8/2007 | Twomey | A61B 5/1072 606/102 |
| 7,442,196 B2 | 10/2008 | Fisher et al. | |
| 7,451,550 B2 | 11/2008 | Dees, Jr. | |
| 7,488,324 B1 * | 2/2009 | Metzger | A61B 17/155 33/511 |
| 7,578,821 B2 | 8/2009 | Fisher et al. | |
| 9,050,197 B2 | 6/2015 | Lorio et al. | |
| 2007/0244488 A1 | 10/2007 | Metzger et al. | |
| 2008/0161815 A1 | 7/2008 | Schoenefeld et al. | |
| 2009/0287310 A1 | 11/2009 | Fisher et al. | |
| 2010/0185203 A1 * | 7/2010 | Haines | A61B 17/155 606/88 |
| 2014/0025081 A1 | 1/2014 | Lorio et al. | |

OTHER PUBLICATIONS

"U.S. Appl. No. 13/555,304, Final Office Action mailed Dec. 15, 2014", 9 pgs.
"U.S. Appl. No. 13/555,304, Non Final Office Action mailed Jun. 19, 2014", 13 pgs.
"U.S. Appl. No. 13/555,304, Notice of Allowance mailed Feb. 4, 2015", 5 pgs.
"U.S. Appl. No. 13/555,304, Response filed Jan. 20, 15 to Final Office Action mailed Dec. 15, 2014", 5 pgs.
"U.S. Appl. No. 13/555,304, Response filed May 23, 2014 to Restriction Requirement mailed Apr. 28, 2014", 2 pgs.
"U.S. Appl. No. 13/555,304, Response filed Sep. 19, 2014 to Non Final Office Action mailed Jun. 19, 2014", 7 pgs.
"U.S. Appl. No. 13/555,304, Restriction Requirement mailed Apr. 28, 2014", 9 pgs.
"Libra Dynamic Knee Balancer", [Online]. Retrieved from the Internet: <synvasive.com>, (Jan. 2010), 3 pgs.
"Microplasty® Total Knee Instrumentation, Surgical Technique, Vanguard Complete Knee System", Biomet Orthopedic, (Jun. 25, 2011), 1-51.
"Vanguard@ Complete Knee System", Design Rationale, Bioment Orthopedic, (May 15, 2011), 1-31.
"Vanguard@ Premier Instrumentation CR or PS Surgical Technique", Biomet Orthopedic, (2011), 1-36.
Peyton, Randy, et al., "Calibrated Knee Tensor and Method of Use", Research Disclosure 483, (Jul. 2004), 1 pg.

* cited by examiner

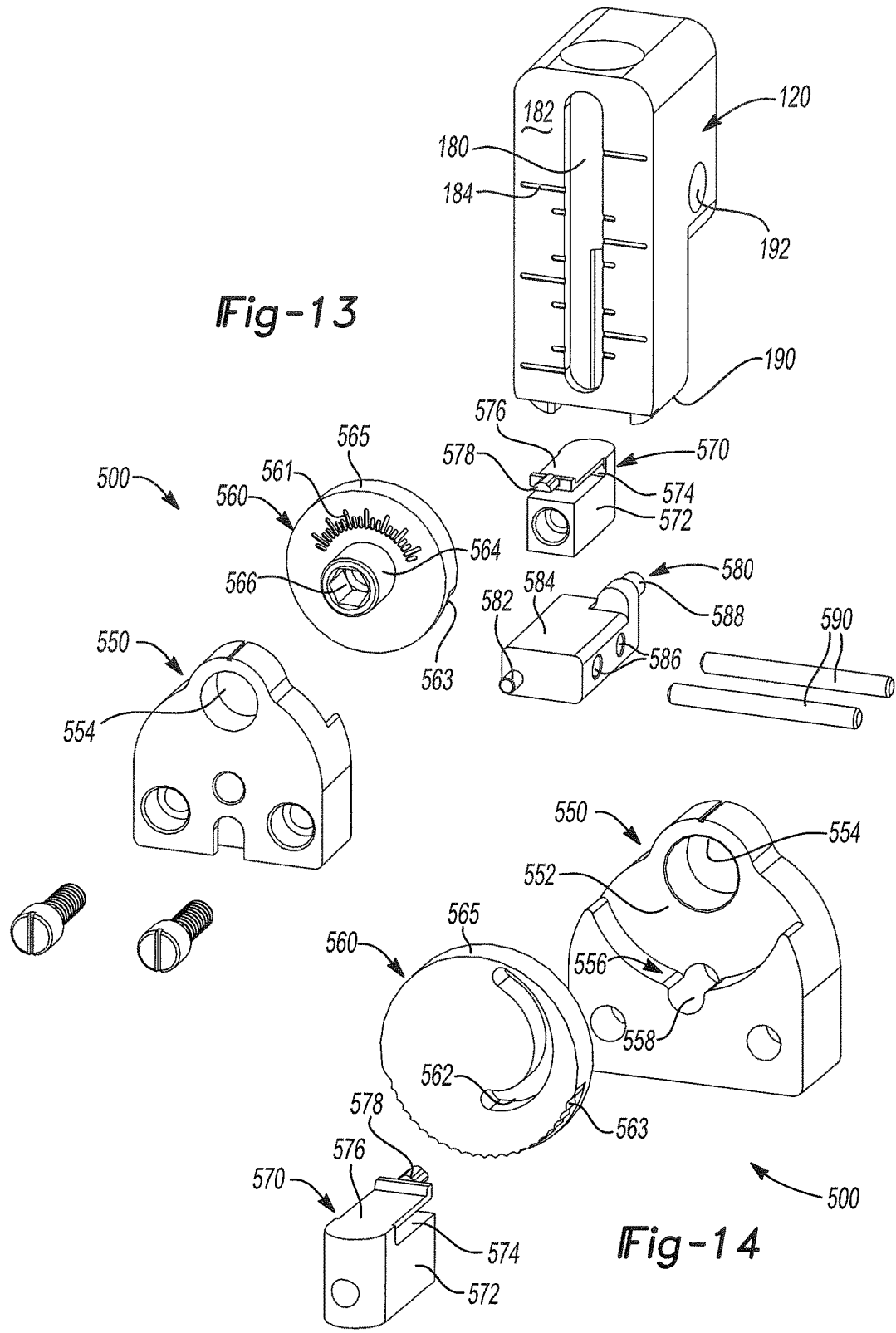

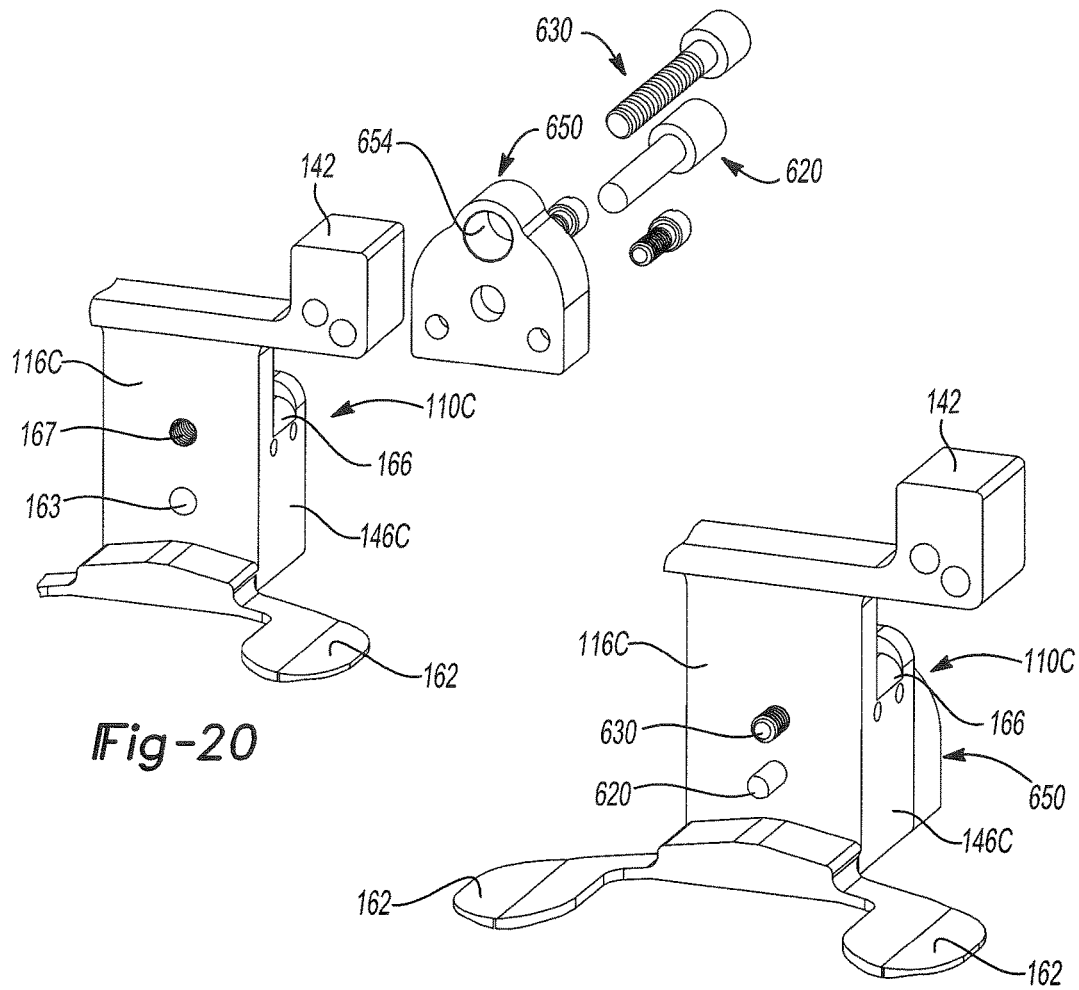
Fig-20
Fig-21
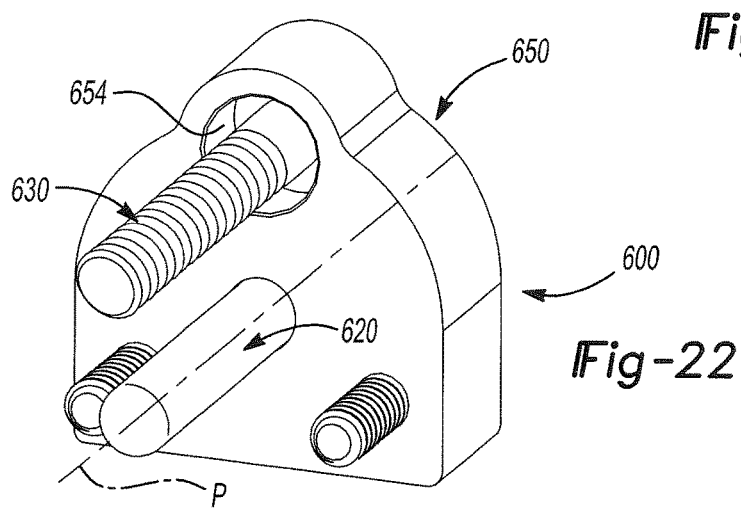
Fig-22

KNEE SIZING AND BALANCING INSTRUMENT

CROSS-REFERENCE TO RELATED APPLICATION

This application is a continuation of U.S. patent application Ser. No. 13/555,304 filed on Jul. 23, 2012, the entire disclosure of which is incorporated herein by reference.

FIELD

The present disclosure relates to an integrated knee sizing and balancing instrument and associated methods.

INTRODUCTION

During knee arthroplasty various sizing, balancing and trialing procedures are performed before an implant is selected and/or implanted. For example, the femoral component is carefully sized and the anterior-posterior dimension of the resected distal femur is determined using an anterior-posterior (AP) sizer. Additionally, knee balancing is performed to achieve equal flexion gaps and proper tension of the medial and lateral ligaments using a knee tensor or balancer.

SUMMARY

This section provides a general summary of the disclosure, and is not a comprehensive disclosure of its full scope or all of its features.

The present teachings provide an orthopedic instrument for knee arthroplasty that is configured to combine anterior-posterior (AP) femoral sizing and tension and balancing of the ligaments of a patient's knee in one synergistically integrated orthopedic instrument rather than using two separate instruments. In some embodiments the orthopedic instrument is unilateral, i.e., right/left knee specific. In some embodiments, the orthopedic instrument is universal and can be used for both a right and a left knee.

In some embodiments, the orthopedic instrument includes an anterior-posterior (AP) sizer assembly, a tensor assembly and a rotation mechanism. The sizer assembly includes a stylus, a sizer body including medial and lateral posterior feet extending substantially perpendicularly from the sizer body, and a sizer slider that can slide relative to the sizer body along a medial-lateral direction relative to a patient's knee for femoral sizing. The tensor assembly includes a tensor frame having a central portion, medial and lateral wings extending at an angle from the central portion, and medial and lateral posterior feet extending substantially perpendicularly to the central portion. The rotation mechanism includes a portion coupled to the tensor frame of the tensor assembly and a portion coupled to the sizer body. The rotation mechanism is configured to rotate the medial and lateral posterior feet of the sizer body relative to the tensor frame toward a lateral side of the patient's knee for balancing and tensioning the knee ligaments.

In some embodiments, the rotation mechanism is configured to be left/right knee specific (unilateral). In some embodiments, the rotation mechanism is configured to be universal for both right and left knees. Two embodiments of the rotation mechanism of the universal integrated orthopedic instruments are provided.

In some embodiments, the orthopedic instrument is universal and includes an anterior-posterior sizer assembly and a tensor assembly. The sizer assembly includes a stylus, a sizer body having medial and lateral posterior feet extending substantially perpendicularly from the sizer body, and a sizer slider slidable relative to the sizer body along a medial-lateral direction relative to a patient's knee. The sizer body has a channel therethrough. The tensor assembly includes a tensor frame having a central portion, medial and lateral wings extending at an angle from of the central portion, a tab extending from the central portion between the medial and lateral wings and having an elongated aperture, and medial and lateral posterior feet extending substantially perpendicularly to the central portion. The orthopedic instrument also includes a plate having an angular scale on a first side and a recess on a second side opposite to the first side and facing the sizer body. The orthopedic instrument also includes a knob rotatably received in the recess of the plate. The knob has a cam groove on a side facing the sizer body, and a cam slider supported in the channel of the sizer body and slidable in a medial-lateral direction within the channel of the sizer body. The cam slider includes a first post guidable by the cam groove of the knob and a second post movably received in the elongated aperture of the tensor frame. Rotating the knob rotates the sizer body relative to the tensor frame and changes a relative gap between the corresponding posterior feet of the sizer body and the tensor frame to tension the ligaments and balance the knee.

The present teachings also provide a method of sizing and balancing a knee for arthroplasty. The method includes placing an integrated orthopedic instrument for femoral sizing and ligament balancing in contact with a resected distal femoral surface of a femur of a patient's knee in flexion, such that medial and lateral posterior feet of a tensor frame of the instrument are in contact with corresponding posterior condyles of the patient's femur and such that medial and lateral posterior feet of a sizer body of the instrument are positioned on a spacer placed on a resected proximal surface of the patient's tibia. The method includes securing first and second wings extending from a central portion of the tensor frame on the resected distal femoral surface and rotating the sizer body relative to the tensor frame via a rotation mechanism that connects the sizer body and the tensor frame to balance the patient's ligaments in tension. The method includes sizing the patient's femur by moving a stylus movably coupled to the sizer body on an anterior surface of the patient's femur.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 13 is a detail of the exploded view of FIG. 12;

FIG. 14 is a detail of the exploded view of FIG. 11;

FIG. 20 is an exploded view of a detail of the universal integrated orthopedic instrument of FIG. 18;

FIG. 21 is an assembled view of the detail of FIG. 20; and

FIG. 22 is an isometric view of a detail of the universal integrated orthopedic instrument of FIG. 18.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The present teachings are directed to various embodiments of an integrated orthopedic instrument that can function and achieve the objectives of both an AP sizer and a knee balancer in a single construct configured as an integrated, synergetic and enhanced construct that replaces two separate instruments for sizing and balancing. In some embodiments the orthopedic instrument is unilateral, i.e., right/left knee specific. In some embodiments, the integrated orthopedic instrument is universal and can be used for both a right and a left knee.

Figure 7:
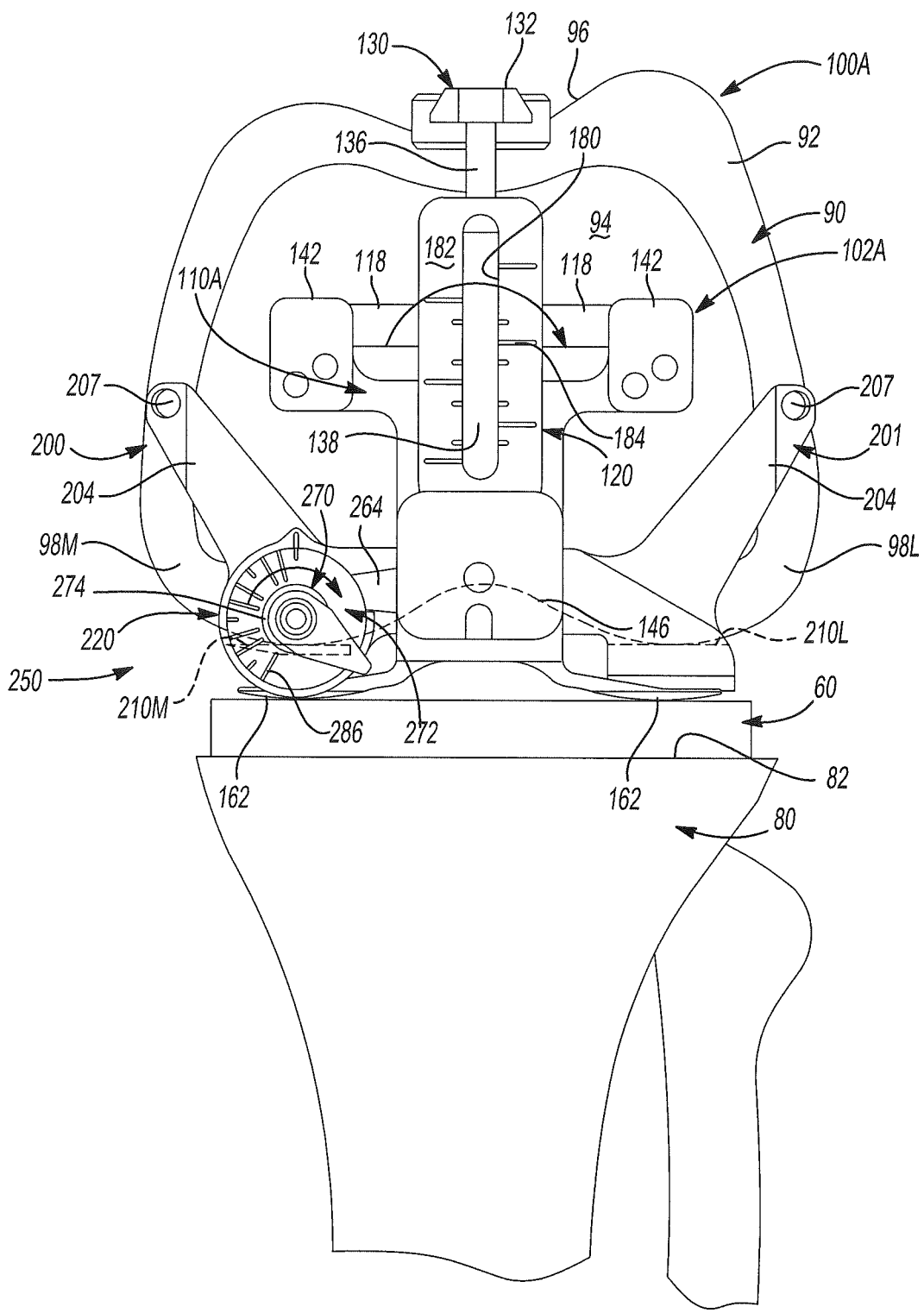
FIG. 7 is an environmental coronal view of the unilateral integrated orthopedic instrument of FIG. 1 shown on a left knee in flexion.
Figure 8:
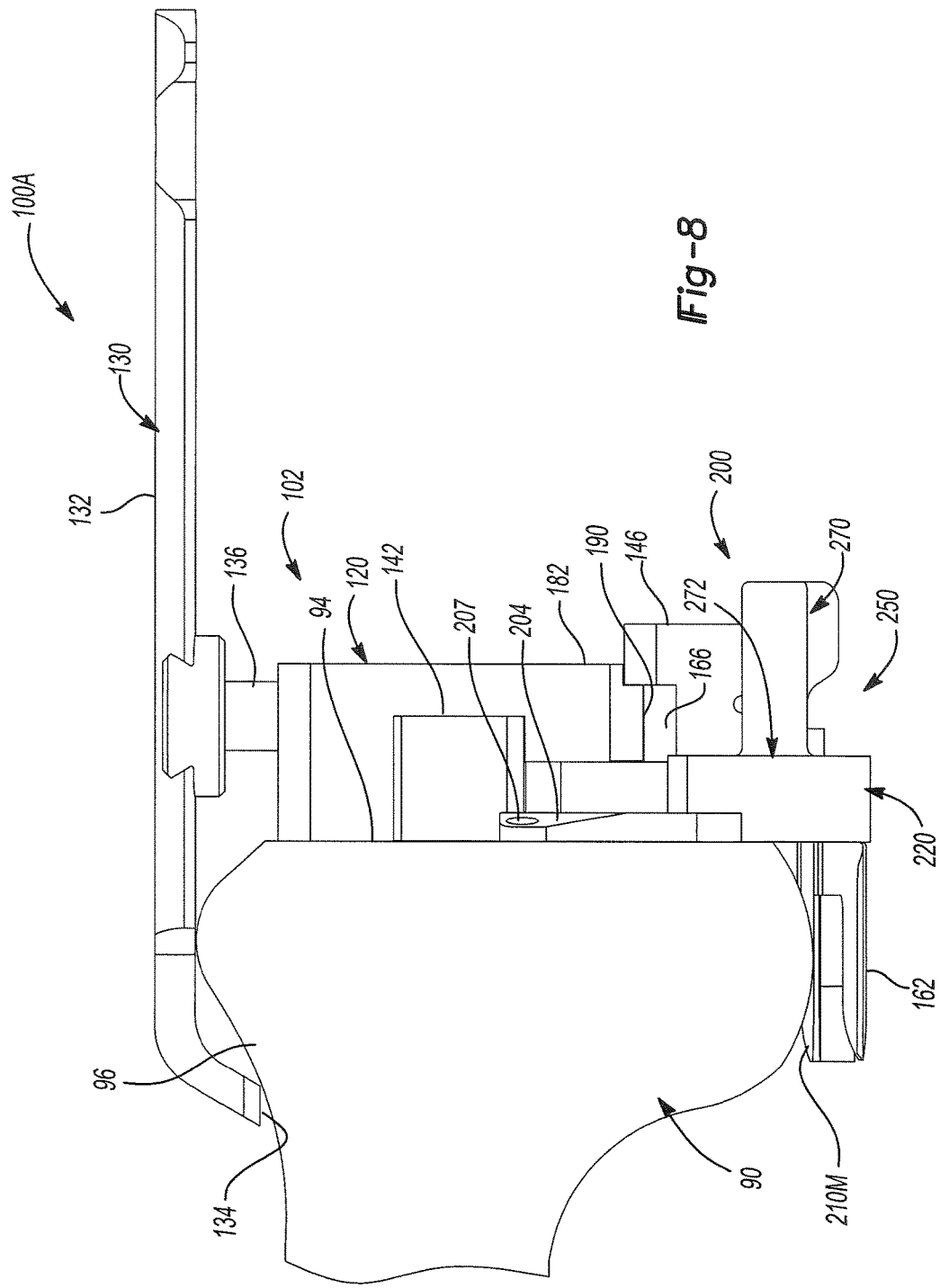
FIG. 8 is an environmental sagittal view of the unilateral integrated orthopedic instrument of FIG. 1 shown on a left knee in flexion.
Figure 16:
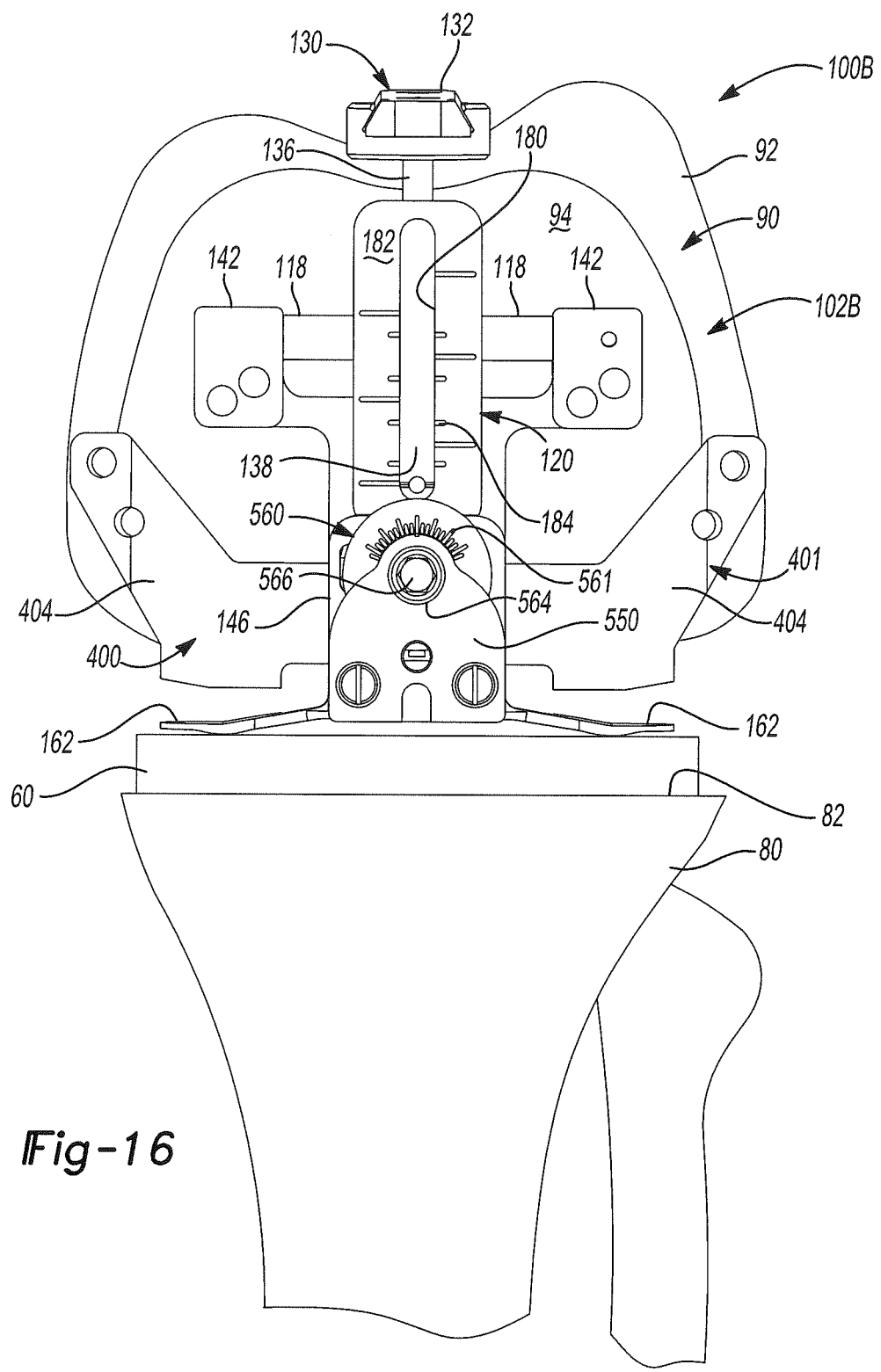
FIG. 16 is an environmental coronal view of the universal integrated orthopedic instrument of FIG. 9 shown on a left knee in flexion.
Figure 17:
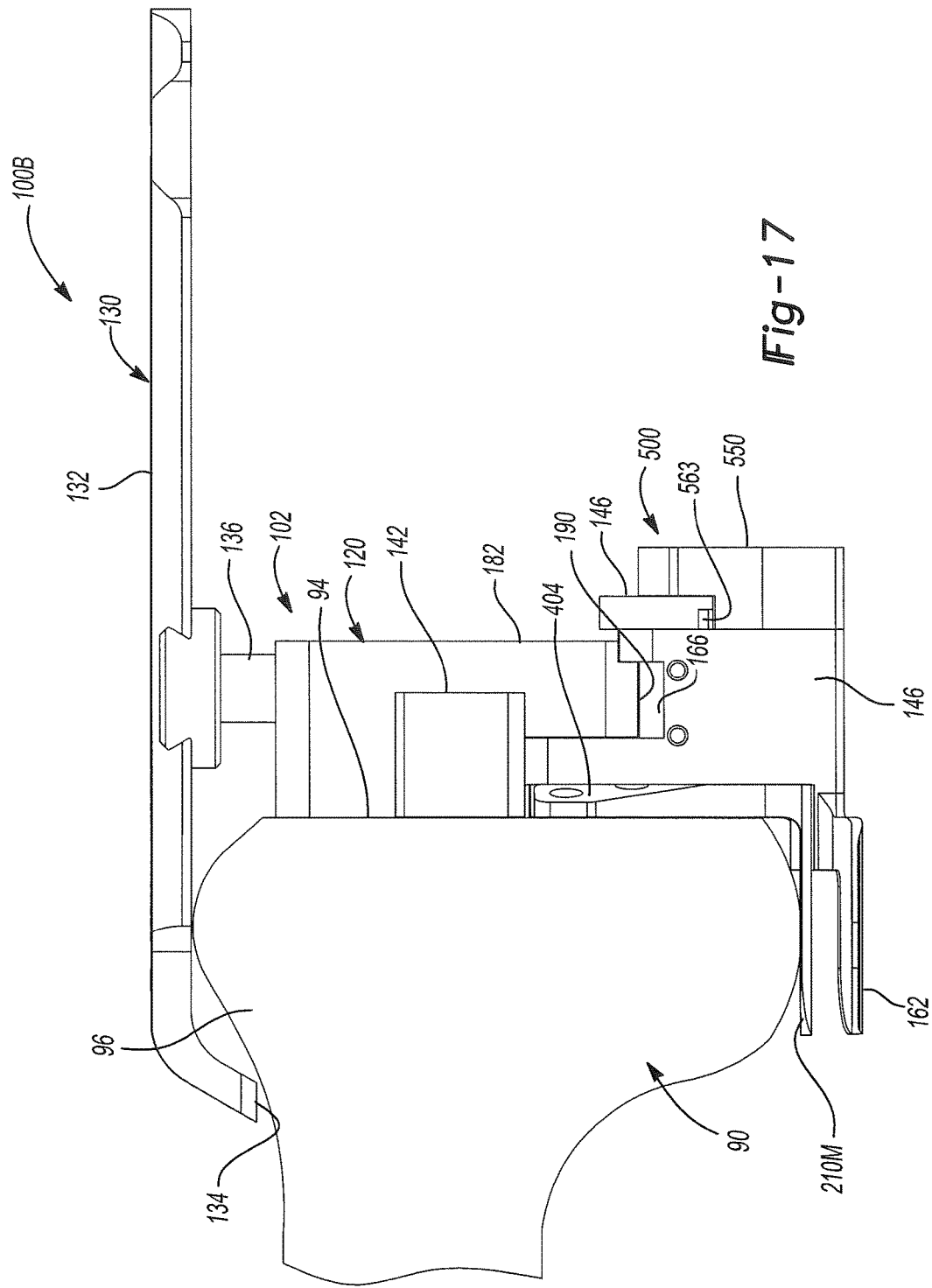
FIG. 17 is an environmental sagittal view of the universal integrated orthopedic instrument of FIG. 9 shown on a left knee in flexion.
Figure 18:
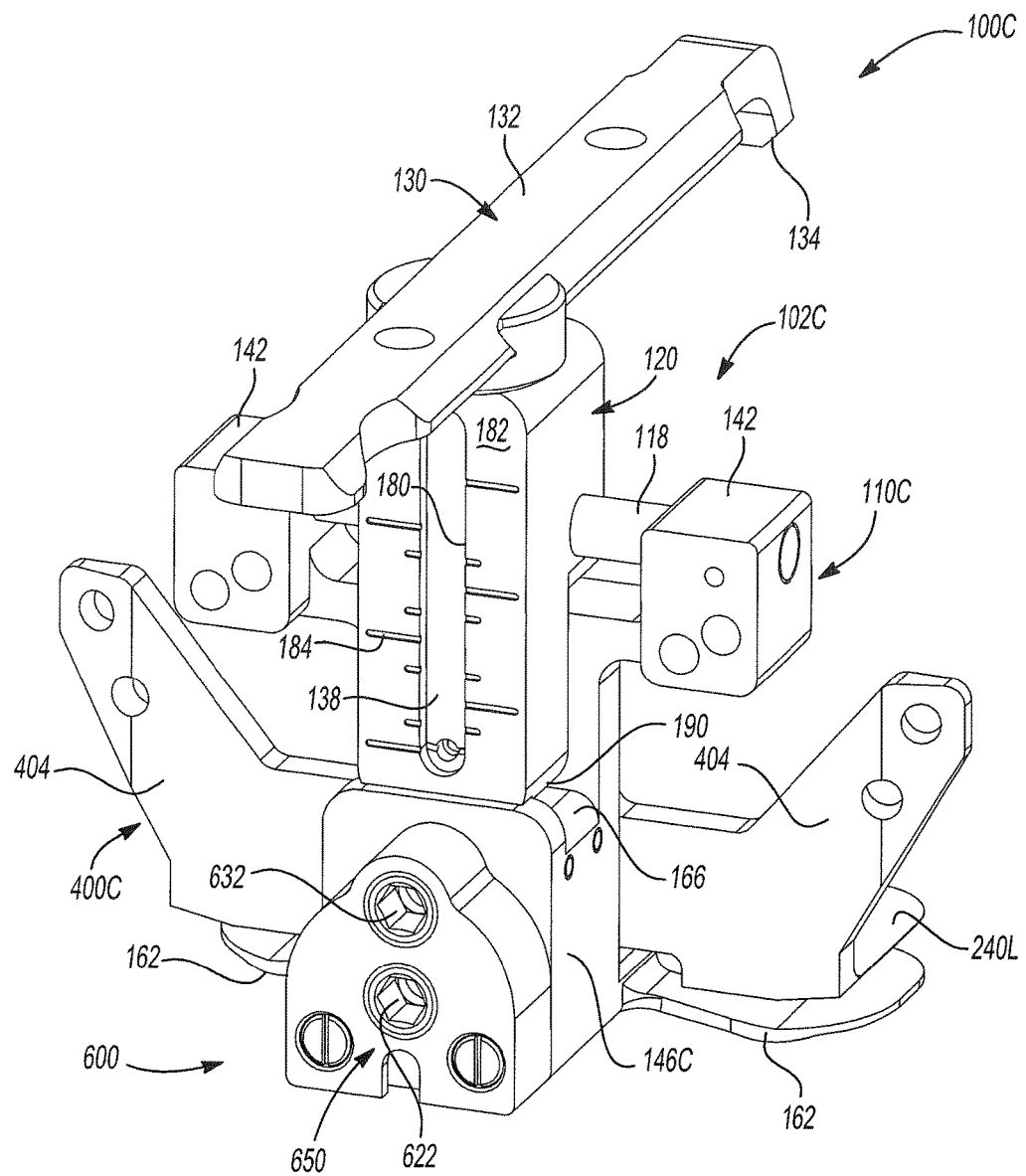
FIG. 18 is a first isometric view of another universal integrated orthopedic instrument according to the present teachings.
Figure 19:
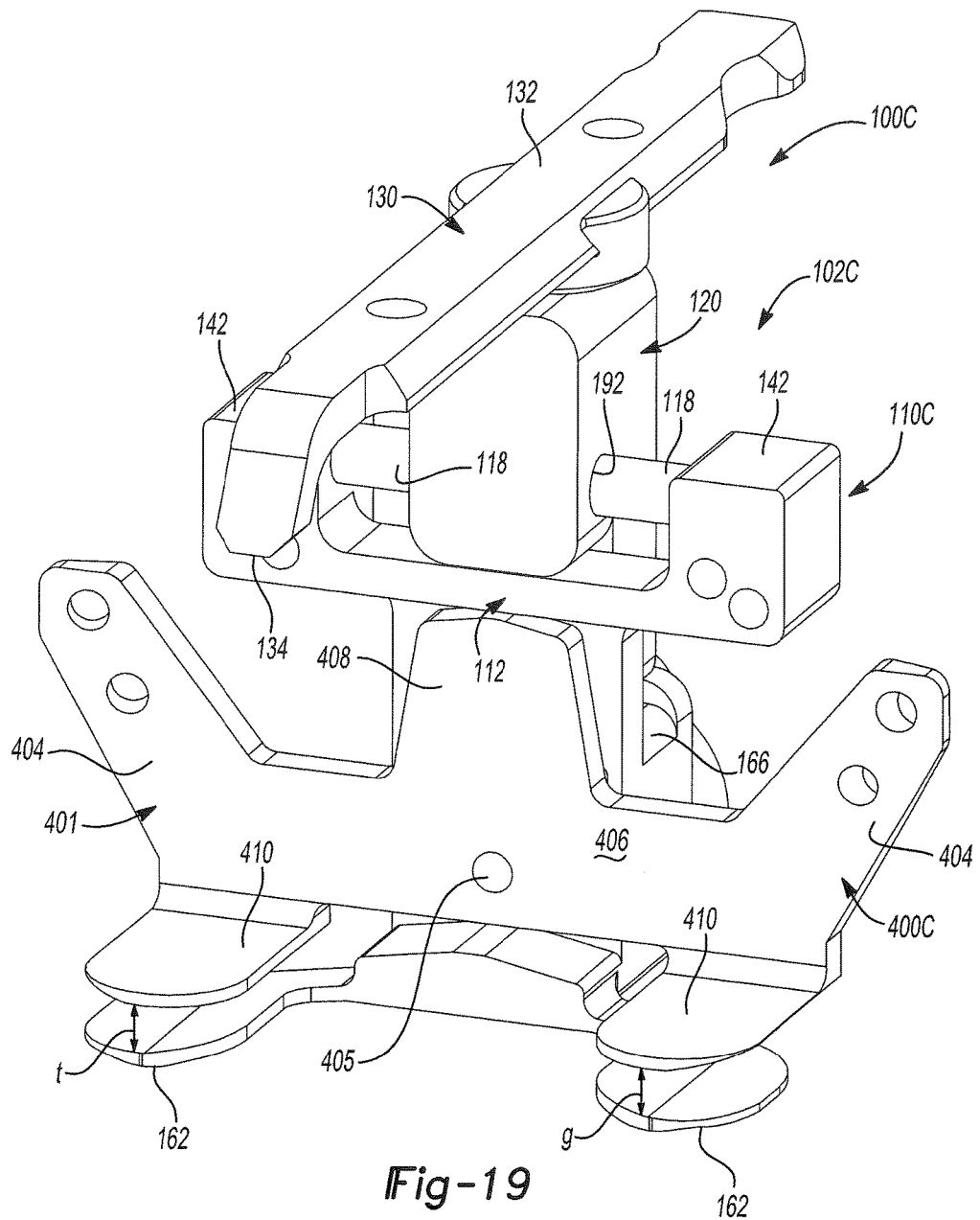
FIG. 19 is a second isometric view of the universal integrated orthopedic instrument of FIG. 18.

More specifically, FIGS. 1-8 illustrate various views and details of an exemplary embodiment of an integrated orthopedic instrument 100A. The integrated orthopedic instrument 100A is unilateral, i.e., configured to be specific to a right or a left knee. The unilateral integrated orthopedic instrument 100A is illustrated for the left knee. The unilateral integrated orthopedic instrument 100A for the right knee is a mirror image of the unilateral integrated orthopedic instrument 100A for the left knee. FIGS. 9-17 illustrate various views and details of another exemplary embodiment of an integrated orthopedic instrument 100B. The integrated orthopedic instrument 100B is universal, i.e., configured to be used with both a right knee and a left knee. FIGS. 18-22 illustrate various views and details of another exemplary universal integrated orthopedic instrument 100C. FIGS. 7 and 8 are environmental views of the unilateral integrated orthopedic instrument 100A shown on a knee in flexion. FIGS. 16 and 17 are environmental views of the universal integrated orthopedic instrument 100B shown on a knee in flexion.

The unilateral and universal integrated orthopedic instruments 100A, 100B, 100C have many elements in common. The common elements will be referenced with the same numerals and will generally be described only once in reference to the unilateral integrated orthopedic instrument 100A. For example, the sizer stylus is referenced by the numeral 130 in both the unilateral integrated orthopedic instrument 100A and the universal integrated orthopedic instruments 100B and 100C.

Referring to FIGS. 1-8, the unilateral integrated orthopedic instrument 100A includes an AP (anterior-posterior) sizer assembly 102A for sizing the femur and a tensor (or balancer) assembly 200 for tensioning the ligaments and balancing the knee. The AP sizer assembly 102A is rotatably coupled to the tensor assembly 200 via a coupling rotation mechanism 250.

The AP sizer assembly 102A can include a sizer body 110A, a sizer slider 120 and a sizer stylus 130. The sizer body 110A has an upper portion 112 and a lower portion 116. The upper portion 112 can be U-shaped and include two pads 142. A rod 118 extends between the pads 142 and is spaced apart from the upper portion 112. The rod 118 may be modularly connected to the pads 142 such that the rod 118 can be detached and re-attached to the sizer body 110A by methods known in the art, such as removable fasteners, press-fitting, taper connections, etc. The pads 142 and the lower portion 116 form a planar surface 150 that can contact and engage a resected surface 94 of a distal end 92 of a femur 90 for anterior-posterior sizing of the femur 90. A base 146 extends from the lower portion 116 of the sizer body 110A. The base 146 defines a U-shaped recess 166 substantially parallel to the rod 118 and a channel 170 perpendicular to the recess 166. The channel 170 is configured for connection with the rotation mechanism 250 as discussed below. The sizer body 110A includes a support portion 160 having first and second (medial and lateral) posterior feet or paddles 162 configured to contact and engage a spacer block 60 positioned on a resected surface 82 of a tibia 80 during the procedure, as shown in FIG. 7. The first and second posterior feet 162 of the sizer assembly 102A have equal thickness.

With continued reference to FIGS. 1-8, the sizer slider 120 of the AP sizer assembly 102A has an L-shaped profile and a longitudinal bore 180. The sizer stylus 130 includes a stylus arm 132 terminating in a stylus tip 134. The stylus arm 132 is coupled to a post 136 with an optional sleeve 138. The post 136 is slidably and rotatably received in the longitudinal bore 180. The stylus arm 132 can rotate about the bore 180 with the post 136 or relatively to the post 136, such that the stylus tip 134 can be brought in contact with any point on an anterior surface 96 of the femur 90 for determining the size of the distal end 92 of the femur 90. The sizer stylus 130 can slide axially with the sizer slider 120 in the medial-lateral direction along the rod 118 to prevent soft tissue impingement during sizing, especially in the anterior-lateral corner, and to provide working space and clearance especially during small incision knee procedures. A projection 190 of the sizer slider 120 is received in the recess 166 of the sizer body 110A for sliding contact thereon. The sizer slider 120 also includes a through-hole 192 receiving the rod 118. The sizer slider 120 can slide along the rod 118 along a track defined by the recess 166. A calibrated linear scale 184 may be marked, or imprinted, or otherwise affixed on a front face 182 of the sizer slider 120.

Referring to FIGS. 1-8, the tensor assembly 200 includes a tensor frame 201 with a central portion 202 and first and second wings 204 extending from and at an angle relative to the central portion 202. The central portion 202 and the first and second wings 204 define a substantially planar surface 206 configured to contact the resected surface 94 of the distal end 92 of the femur 90 and be coplanar with the surface 150 of the sizer body 110A, as shown in FIG. 8. First and second (medial and lateral) posterior feet or paddles 210M, 210L extend from the tensor frame 201 substantially perpendicularly to the planar surface 206. The posterior feet 210L, 210M of the tensor assembly 200 have different thicknesses. Specifically, the lateral posterior foot 210L has a greater thickness "t" that the thickness of the medial posterior foot 210M, such that in the assembled unilateral integrated orthopedic instrument 100A, there is a gap "g" between the medial posterior foot 162 of the sizer assembly 102A and the medial posterior foot of the tensor assembly 200. The gap g allows tensioning and balancing of the knee ligaments when the sizer body 110A is rotated relative to the tensor frame 201 by the rotation mechanism 250.

Referring to FIGS. 3 through 6B, the rotation mechanism 250 includes interacting portions of the tensor frame 201, the sizer body 110A and a cam mechanism that includes first and second cam components 260 and 270. The first cam component 260 includes a cam body 262 and a cam arm 264 extending from the cam body 262 and having a cam post 266. The second cam component (or cam guide) includes a circular plate or dial knob 272 having first and second faces 282, 284 on opposite sides of a curved peripheral wall 288. A shaft or handle 274 extends outward from the second face 284. The first face 282 includes a curved cam groove 276 that receives and guides the cam post 266. The second face 284 includes an angular scale 286. The knob 272 includes flute-like or scallop-like formations 278 along a portion of the peripheral wall 288. The tensor frame 201 includes a cam housing 220 extending from the central portion 202 on a side opposite to the medial posterior foot 210M. The cam housing 220 includes a peripheral wall 222 with two curved slots 224 forming a spring with a spring arm 226 with formations 228 that engage the formations 278 of the knob 272. The spring arm 226 stabilizes and provides tactile feedback the position of knob 272 as the knob 272 is rotated toward the lateral side in incremental angles indicated on the angular scale 286. A distal portion of the cam arm 264 is positioned in a cutout space 230 formed between two walls 232, 234 of the housing 220. The cam body 262 of the cam component 260 is received in the channel 170 of the sizer body 110A. Referring to FIGS. 2, 4, 6A and 6B, when the knob 272 is rotated, the cam post 266 moves along the curved cam groove 276 exerting a rotation moment through the arm 264 to the cam body 262 and to the sizer body 110A toward the lateral side, thereby reducing the gap g (FIG. 2) to an amount required to balance ligament tension and equalize the gaps between the lateral and medial posterior condyles 98L, 98M of the knee joint relative to the tibia 70.

Figure 1:
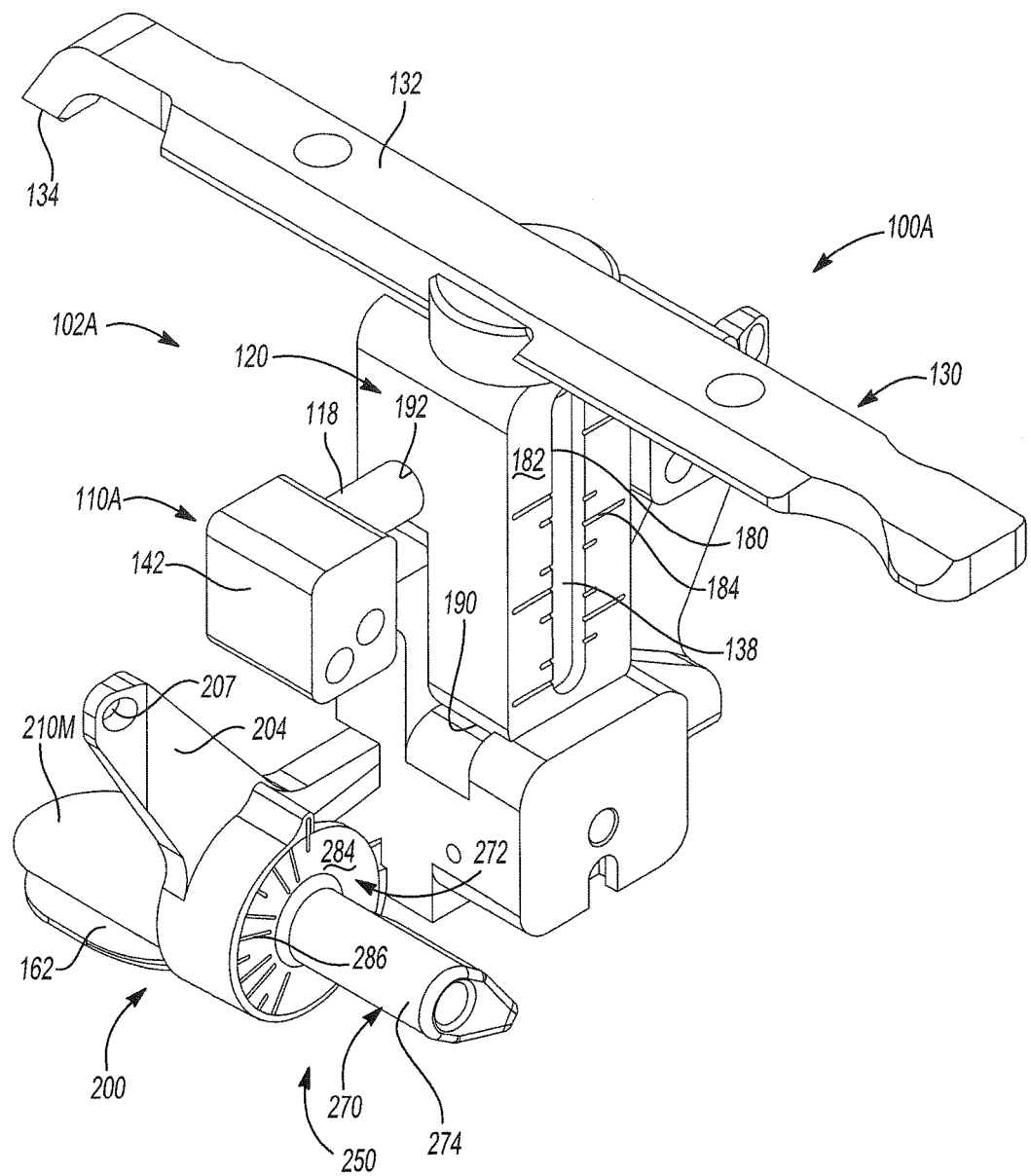
FIG. 1 is a first isometric view of a unilateral integrated orthopedic instrument according to the present teachings.
Figure 2:
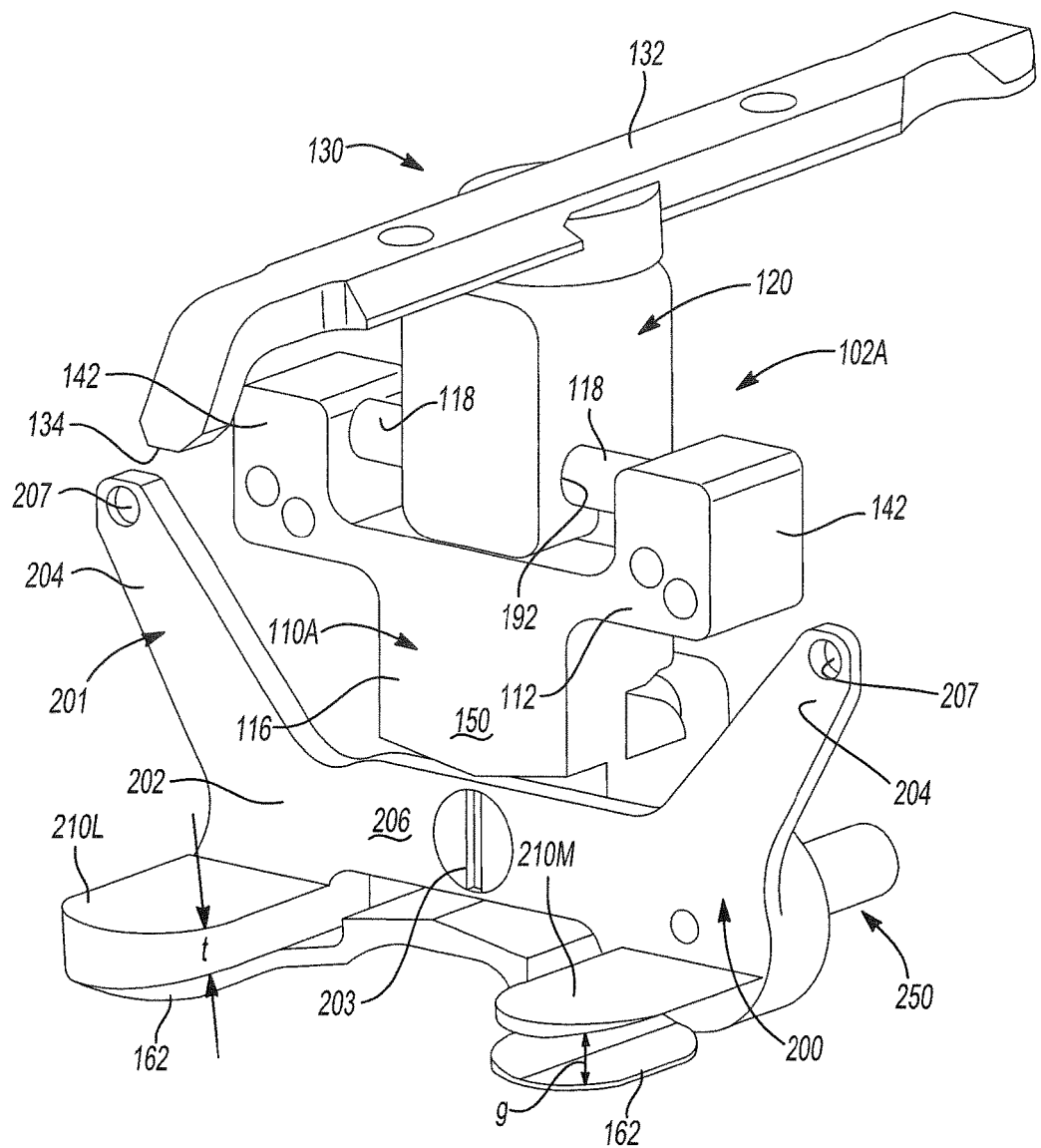
FIG. 2 is a second isometric view of the unilateral integrated orthopedic instrument of FIG. 1.
Figure 3:
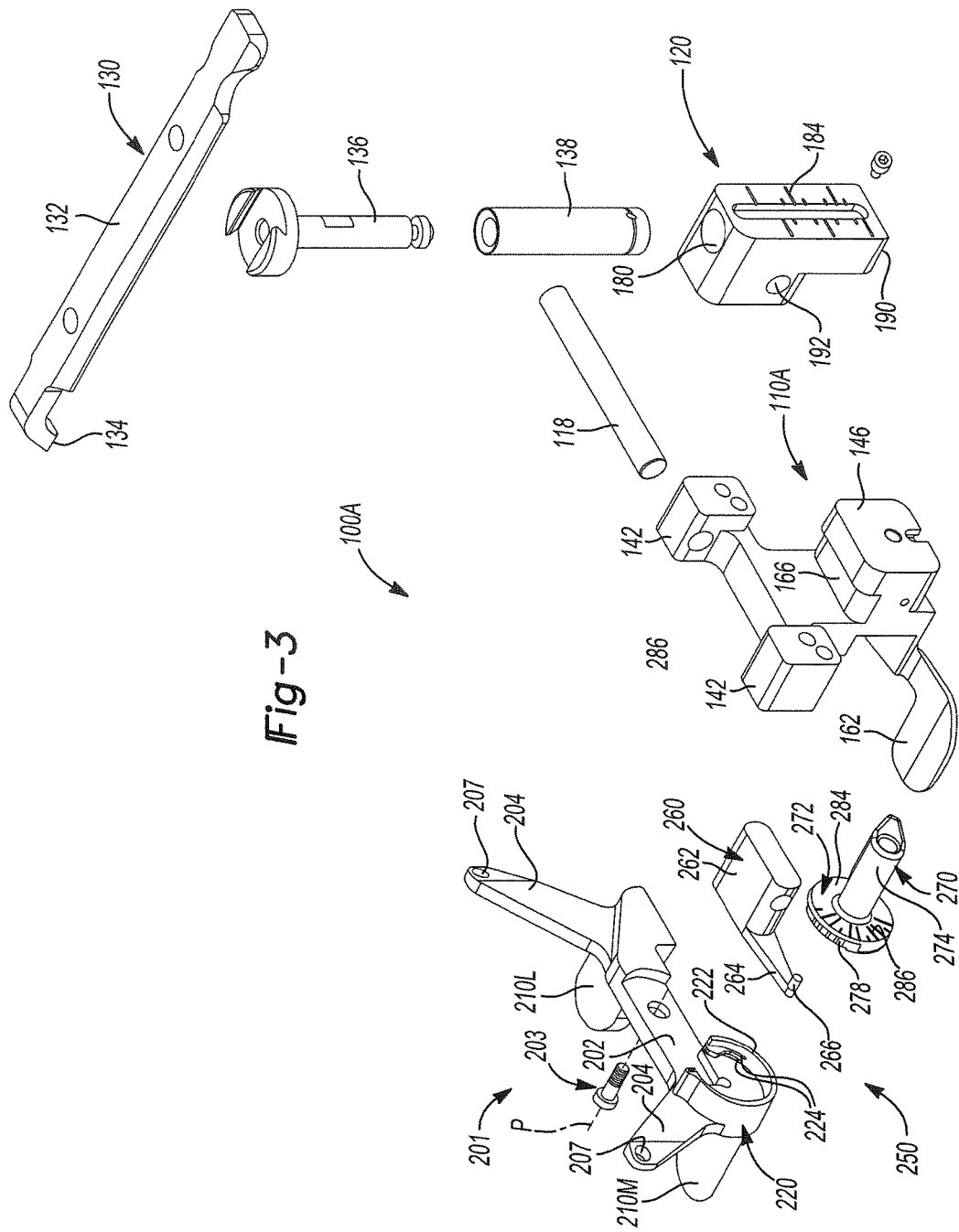
FIG. 3 is an exploded view of the unilateral integrated orthopedic instrument of FIG. 1.
Figure 4:
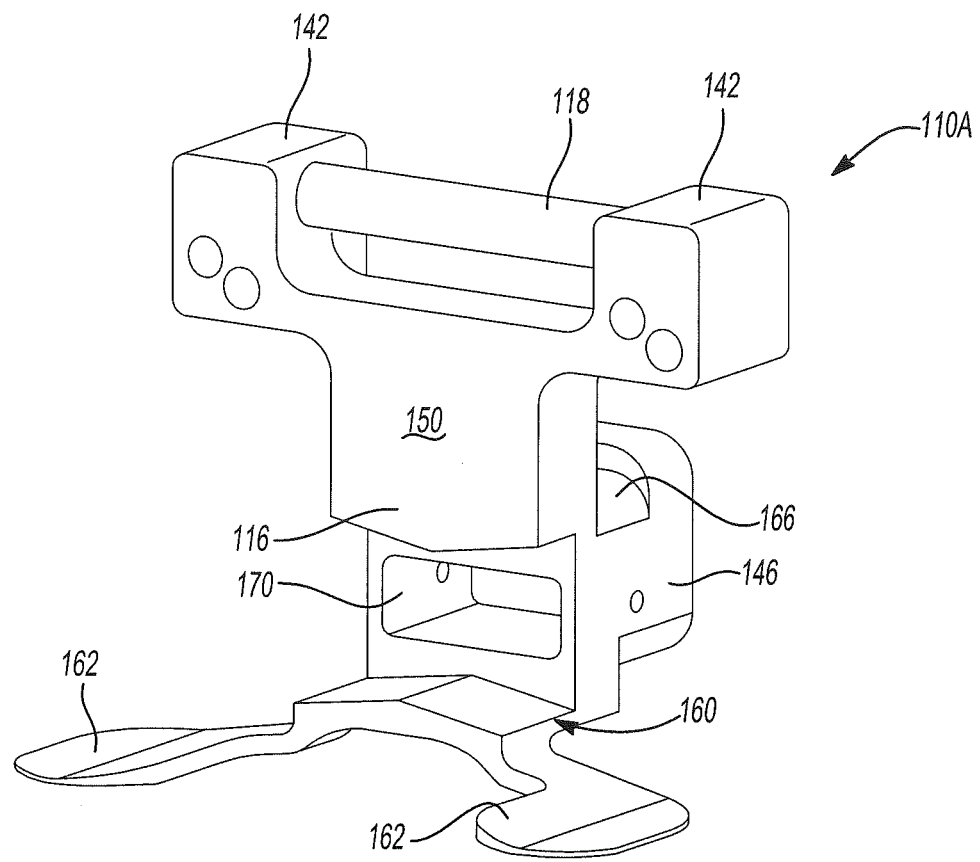
FIG. 4 is an isometric view of a component of a sizer assembly of the unilateral integrated orthopedic instrument of FIG. 1.
Figure 5:
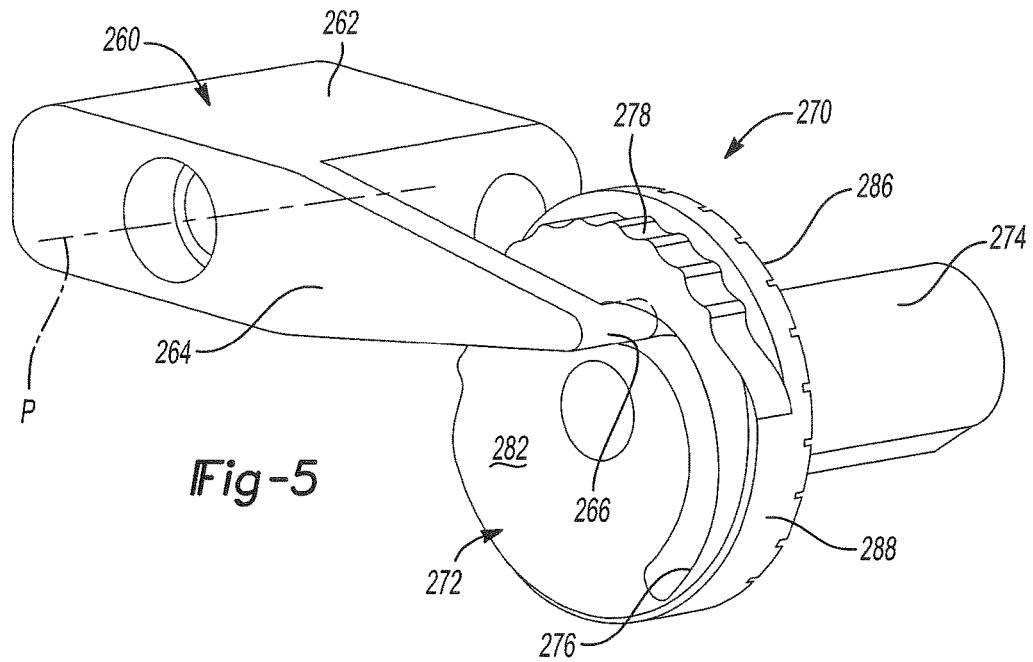
FIG. 5 is an isometric view of a portion of the rotation mechanism of the unilateral integrated orthopedic instrument of FIG. 1.
Figure 6:
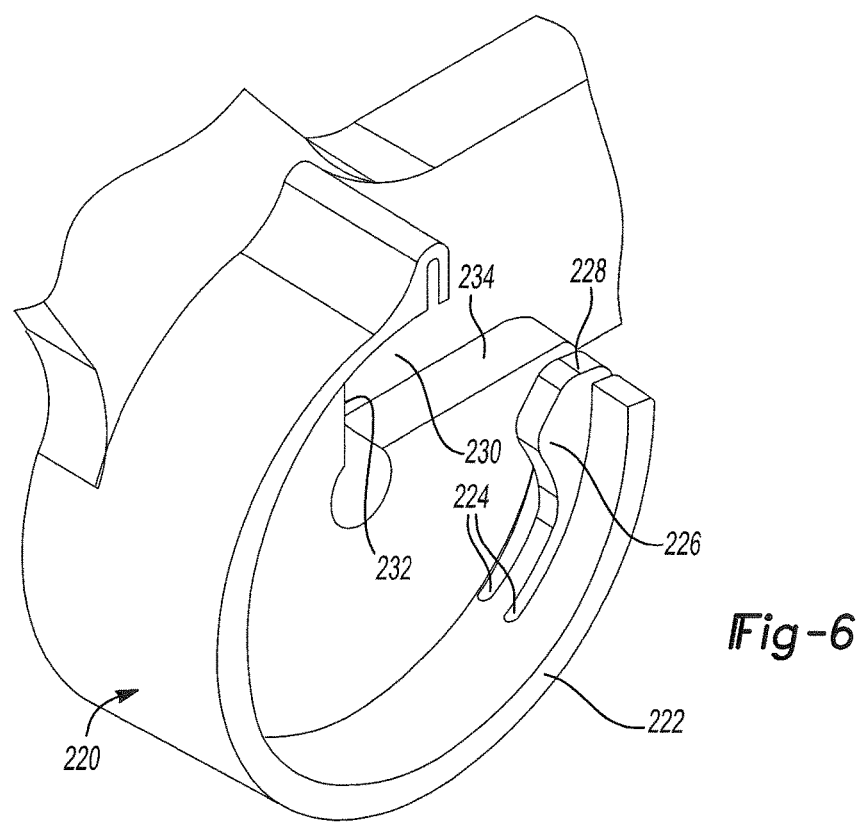
FIG. 6 is an isometric view of a portion of the rotation mechanism of the unilateral integrated orthopedic instrument of FIG. 1.
Figure 6A:
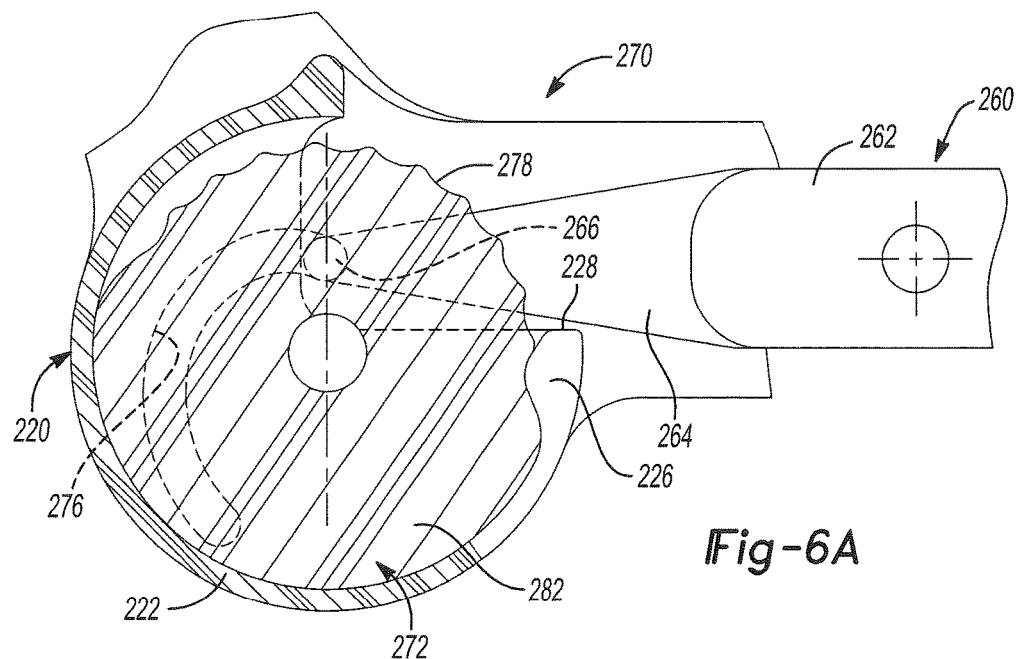
FIG. 6A is a partial sectional view of the rotation mechanism of the unilateral integrated orthopedic instrument of FIG. 1 shown in a first position.
Figure 6B:
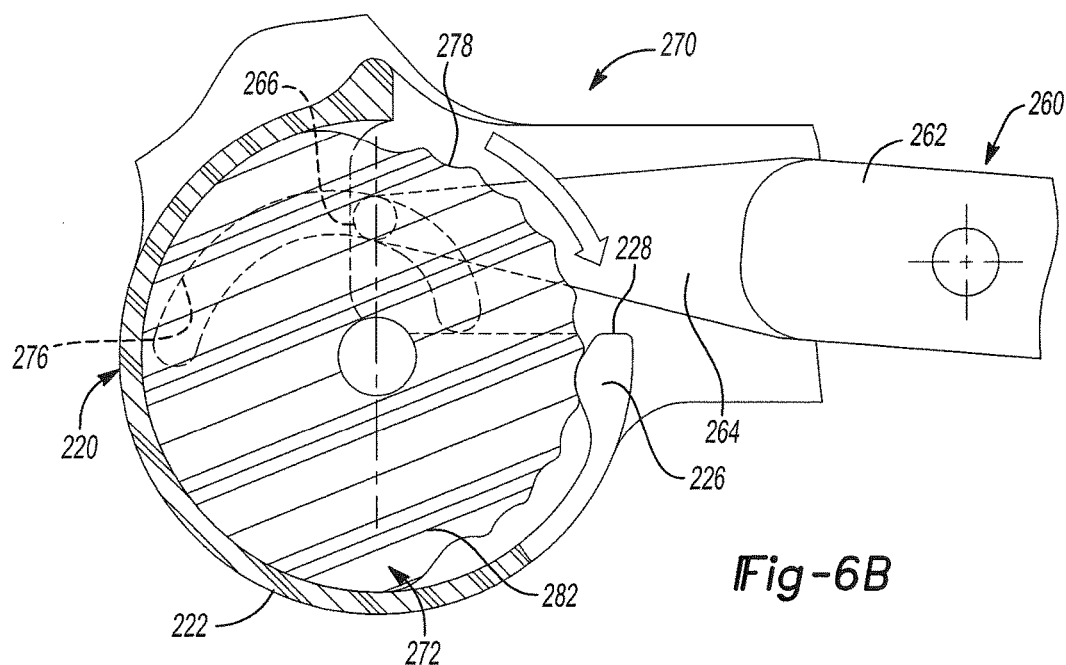
FIG. 6B is a partial sectional view of the rotation mechanism of the unilateral integrated orthopedic instrument of FIG. 1 shown in a second position.

Referring to FIG. 1, the angular scale 286 is calibrated to show the angle of relative rotation between the posterior feet 162 of the AP sizer body 110A and the posterior feet 210M, 210L of the tensor assembly 200, or generally the relative rotation between the sizer body 110A and the tensor frame 201. For example, if the actual rotation angle of the knob 272 is "x" and the relative rotation between the AP sizer body 110A and the tensor frame 201 is "y", then a rotation transmission ratio is equal to "x" divided by "y". In the embodiment of illustrated in FIGS. 1-8, a rotation transmission ratio of about 15 is used. Generally, a rotation transmission ratio of about 5 to about 20 can be used.

Referring to FIGS. 7 and 8, after the distal end 92 of the femur 90 is resected, the unilateral integrated orthopedic instrument 100A is attached to the distal end 92. Specifically, the tensor frame 201 of the tensor assembly 200 is attached to the resected surface 94 of the femur 90 using fasteners through holes 207 in the wings 204. The posterior feet 210M, 210L of the tensor frame 201 are engaged in direct contact with the corresponding medial and lateral posterior condyles 98M, 98L of the femur 90, and the surface 206 of the tensor frame 201 and the surface 150 of the sizer body 110A are in direct contact with the resected surface 94 of the femur 90. The posterior feet 162 of the sizer body 110A are supported on the spacer 60 positioned on the resected surface 82 of the tibia 80. The knob 272 is turned toward the lateral side of the femur 90 such that the sizer body 110A and, in particular, the posterior feet 162 of the sizer body 110A rotate relative to the posterior feet 210M, 210L of the tensor frame 201, (which is attached to the resected surface 94 of the femur 90) about pivot axis P until the ligaments of the knee joint are balanced in tension. The pivot axis P defined by a bolt 203 that rotatably couples the tensor frame 201 and the cam body 262 of the cam component 260. After balancing, the sizer body 110A can also be fixed on the resected surface 94 with fasteners and used to determine the size of the femur 90.

The sizer slider 120 can slide relatively to the sizer body 110A in the medial-lateral direction to avoid tissue impingement during sizing. The arm 132 of the stylus 130 can be rotated, such that the stylus tip 134 contacts the anterior surface 96 of the femur 90. Several readings may be taken on the scale 184 as the stylus tip 134 moves about the anterior surface 96 by observing the position of an indicator (not shown) relative to the scale 184. The size of the femur 90 is determined by the highest reading on the scale 184. During the movement of the stylus 130, the sizer slider 120 may be moved medially or laterally to accommodate the movement of the stylus 130 without causing tissue impingement. It should be noted that femoral sizing can also be done before ligament balancing, or repeated after ligament balancing for an additional confirmation.

Referring to FIGS. 9-17, a first embodiment of the universal integrated orthopedic instrument 100B is illustrated. The universal integrated orthopedic instrument 100B is configured to be used in both the right and left knee instead of using right and left knee unilateral integrated orthopedic instruments, such as the unilateral integrated orthopedic instrument 100A for the left knee and a unilateral integrated orthopedic instrument (mirror image of 100A) for the right knee. The universal integrated orthopedic instrument 100B includes an AP (anterior-posterior) sizer assembly 102B for sizing the femur and a tensor (or balancer) assembly 400 for tensioning the ligaments and balancing the knee. The AP sizer assembly 102B is rotatably coupled to the tensor assembly 400 via a coupling rotation mechanism 500. The AP sizer assembly 102B shares many elements with the AP sizer assembly 102A of the unilateral integrated orthopedic instrument 100A. The elements that are substantially identical are referenced with the same numerals and their description is not repeated. Differences between similar elements will be pointed out.

Figure 9:
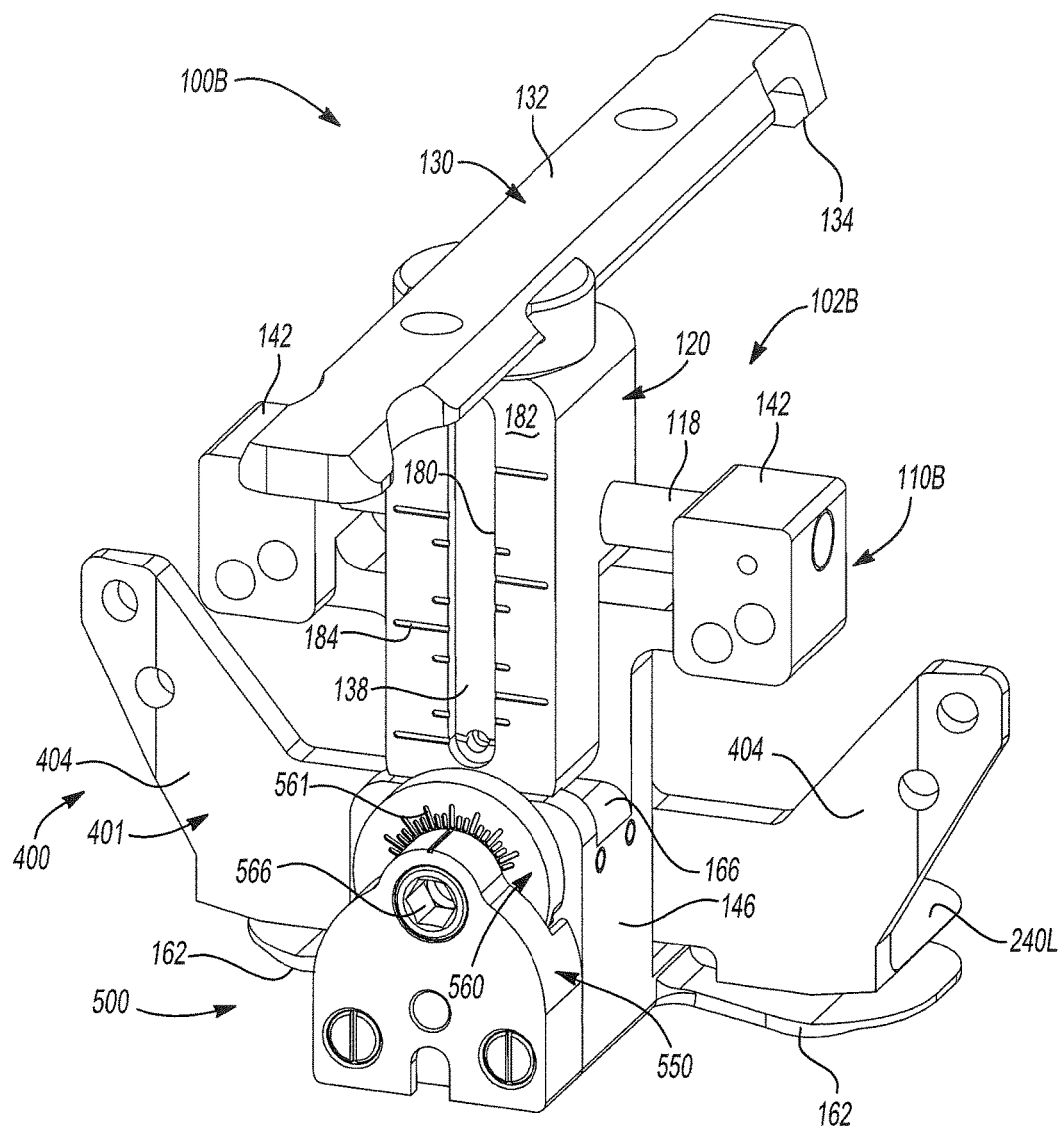
FIG. 9 is a first isometric view of a universal integrated orthopedic instrument according to the present teachings.
Figure 10:
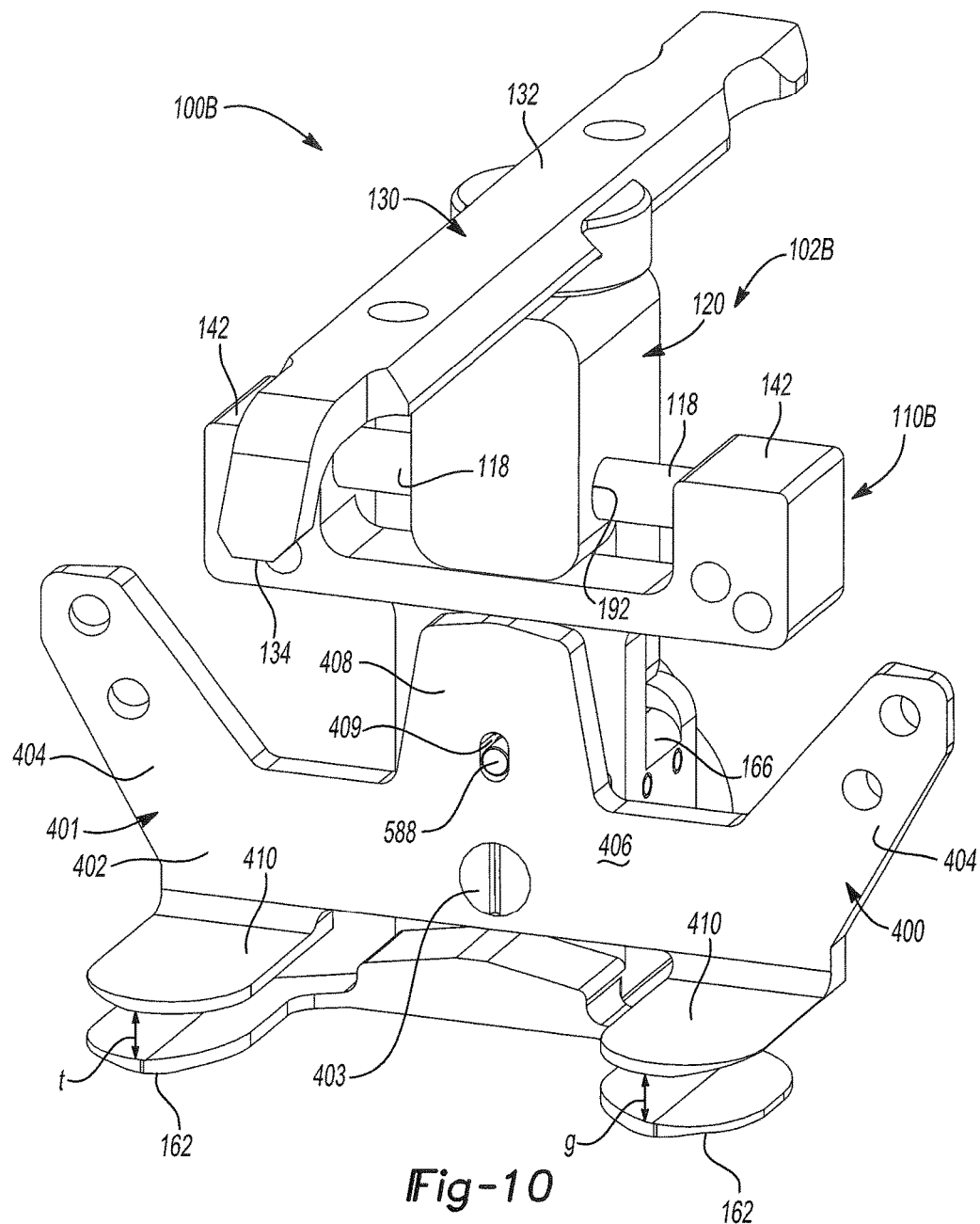
FIG. 10 is a second isometric view of the universal integrated orthopedic instrument of FIG. 9.

Referring to FIGS. 9-17, the tensor assembly 400 includes a tensor frame 401 with a central portion 402, first and second wings 404 extending from and at an angle relative to the central portion 402 and a tab or flange 408 extending from the central portion 402 perpendicularly to the central portion 402 and positioned symmetrically between the first and second wings 404. The central portion 402, the flange 408 and the first and second wings 404 define a substantially planar surface 406 configured to contact the resected surface 94 of the distal end 92 of the femur 90, as shown in FIG. 17. First and second (medial and lateral) posterior feet or paddles 410 extend from the tensor frame 401 substantially perpendicularly to the planar surface 406. Unlike the posterior feet 210M, 210L of the tensor assembly 200 of the unilateral integrated orthopedic instrument 100A, the posterior feet 410 of the tensor assembly 400 have the same thickness. In this respect, equal gaps "g" are formed between the posterior feet 162 of the sizer assembly 102B and the posterior feet of the tensor assembly 400, as shown in FIG. 10. The gaps g allow tensioning and balancing of the knee ligaments when the sizer assembly 102B is rotated relative to the tensor assembly 400 by the rotation mechanism 500 toward the lateral side of the knee joint, whether the universal integrated orthopedic instrument 100B is attached on the left or the right knee of the patient.

The AP sizer assembly 102B can also include a sizer body 110B, a sizer slider 120 and a sizer stylus 130. The sizer body 110B is modified from the sizer body 110A to accommodate the different tensor assembly 400 and rotation mechanism 500 for the universal (right and left knee) use of the universal integrated orthopedic instrument 100B. More specifically, the sizer body 110B has a U-shaped upper portion 112 that includes two pads 142 and a lower portion 116B that is recessed from the upper portion 112. As in the sizer body 110A of the unilateral integrated orthopedic instrument 100A, a rod 118 extends between the pads 142 and is spaced apart from the upper portion 112. Similarly, a base 146 extends from the lower portion 116B of the sizer body 110B. The base defines a U-shaped recess 166 substantially parallel to the rod 118. A channel 170B extends through the sizer body 110B and the base 146 perpendicularly to the recess 166. A projection 190 of the sizer slider 120 is received in the recess 166 for sliding contact thereon. The sizer slider 120 also includes a through-hole 192 receiving the rod 118. The sizer slider 120 can slide along the rod 118 and along a track defined by the recess 166. The channel 170B is configured for connection with the rotation mechanism 500 as discussed below.

Referring to FIGS. 11-15, the rotation mechanism 500 includes a plate 550, a rotatable dial or knob 560, a spring 570, a cam slider 580 and corresponding coupling portions of the tensor frame 401 and the sizer body 110B. The knob 560 includes a curved groove or cam guide 562 that is configured to receive and guide a cam post 582 (first post 582) that extends from a body 584 of the cam slider 580 at an offset (non-symmetrically) relative to the body 584 and toward the knob 560 (see also FIG. 13). The knob 560 includes a shaft 564 with a driver formation 566 configured to engage a driver for rotating the knob 560 and an angular scale 561 (see also FIGS. 12 and 13). The knob 560 also includes flute- or scallop-type formations 563 along a portion of a peripheral wall 565 of the knob 560.

With continued reference to FIGS. 11-15, the plate 550 includes a recess 552 formed substantially as a circular sector and configured for receiving a portion of the knob 560, as shown, for example, in the assembled view of FIG. 9. The recess 552 is bounded by a curved wall portion 556 having a center slot 558 oriented substantially perpendicularly to the plane defined by the body of the plate 550 (see FIG. 14). The shaft 564 of the knob passes through an opening 554 of the plate 550 such that the driver formations 566 are accessible during the procedure.

Figure 11:
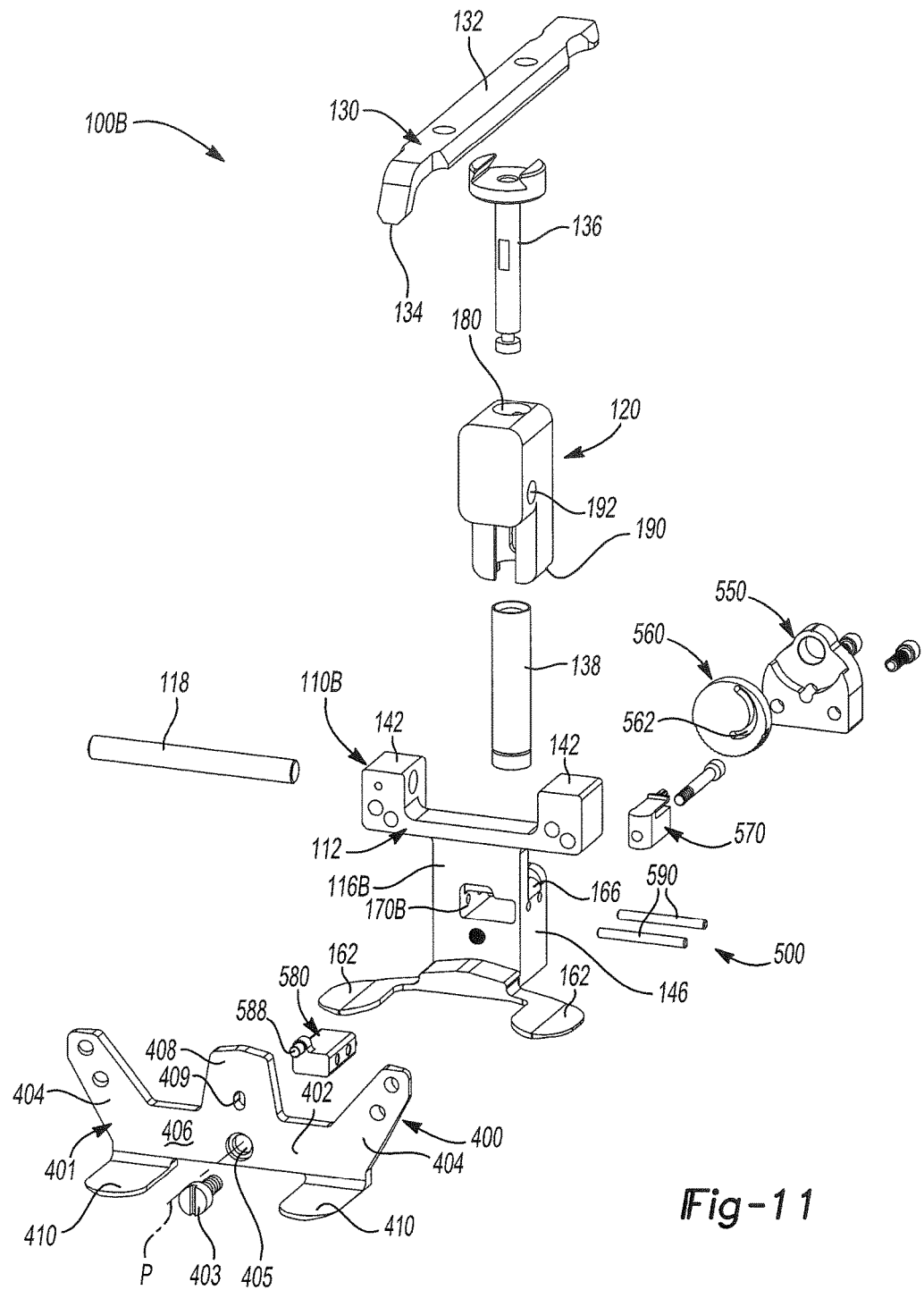
FIG. 11 is an exploded back view of the universal integrated orthopedic instrument of FIG. 9.
Figure 12:
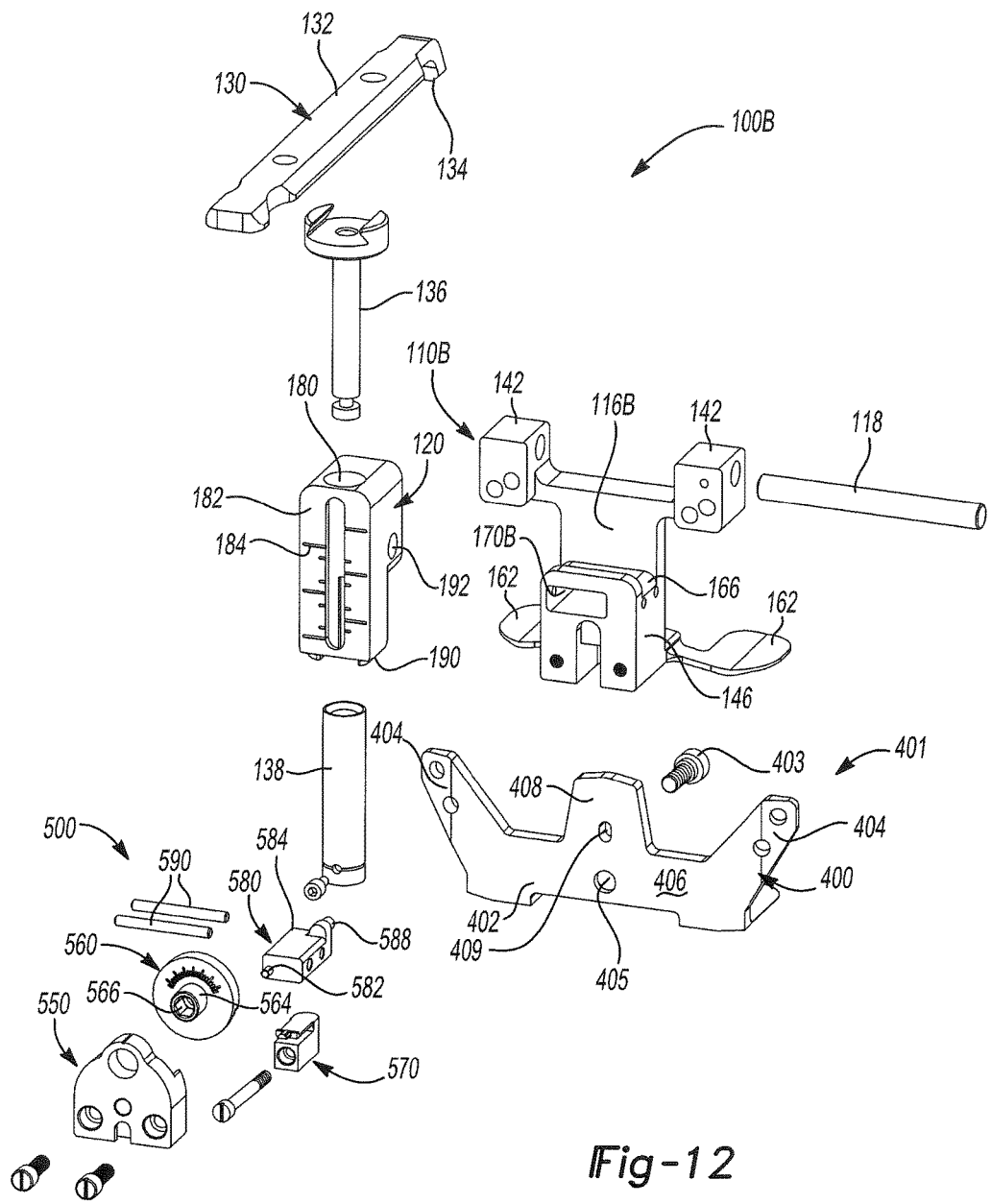
FIG. 12 is an exploded front view of the universal integrated orthopedic instrument of FIG. 9.
Figure 15:
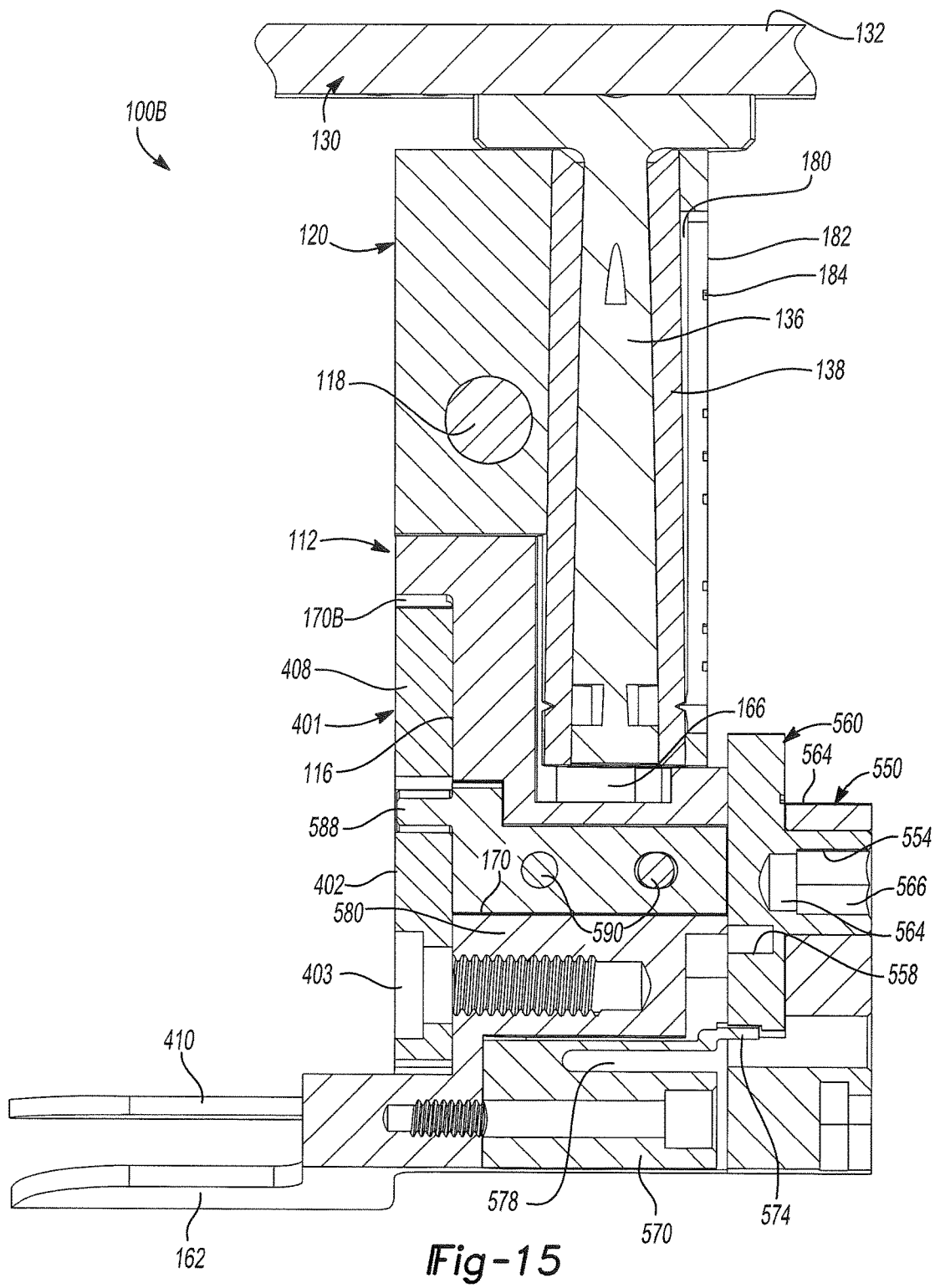
FIG. 15 is a sectional view of the universal integrated orthopedic instrument of FIG. 9.

With continued reference to FIGS. 11-15, the body 584 of the cam slider 580 is configured to be movably received in the channel 170B of the AP sizer body 110B with clearance such that the body 584 of the cam slider 580 can slide along one or more pins or rods 590 that pass through corresponding bores 586 of cam slider 580 (see FIGS. 11 and 13). This degree of freedom contributes to a rotation transmission ratio discussed below. The pins 590 span the medial-lateral width of the channel 170B and are supported on the AP sizer body 110B. A second post 588 having a circular cross-section extends asymmetrically from the slider body 584 toward the tensor frame 401 and is movably received in an elongated aperture 409 of the tensor frame 401. The elongated aperture 409 provides clearance such that the second post 588 can move along the aperture 409 and contributes to the rotation transmission ratio discussed below.

The spring 570 of the rotation mechanism 500 has a body 572 with a slot 574 forming a flexible leaf 576 with a finger 578 extending toward the knob 560, such that the finger 578 can be engaged to and disengaged from the flute formations 563 on the knob 560 and provide resistance and tactile and/or audible feedback when the knob 560 is rotated by the user (see FIG. 14).

Summarizing the operation of the rotation mechanism 500, a driver (not shown) can be used to engage the driver formations 566 of the knob 560 and rotate the knob 560 toward the lateral side of the right or left knee. The medical professional can be guided by the scale 561 and receive a tactile and/or audible feedback, as discussed above, by the interaction of the finger 578 of the spring 570 with the flute formations 563 of the knob 560. The rotation is transmitted from the knob 560 through the cam post 582 to the cam slider 580 and from the cam slider 580 the AP sizer body 110B. The AP sizer body 110B is rotatably coupled to the tensor frame 401 via a pivot bolt 403 defining a pivot axis P that passes through a pivot hole 405. The second post 588 of the cam slider 580 is received in the elongated aperture 409 of the tensor frame 401 such that a moment is transmitted from the second post 588 to rotate the AP sizer body 110B relative to the tensor frame 401. The motion of the cam post 582 of the cam slider 580 along the cam groove 562 of the knob 560, the travel of the cam slider 580 along the pins 590 in the channel 170B of the sizer body 110B, and the travel of the second post 588 along the elongated aperture 409 of the tensor frame 401 of the tensor assembly 400 provide a predetermined rotation transmission ratio between the rotation of the knob 560, and the relative rotation between the posterior feet 162 of the AP sizer body 110B and the posterior feet 410 of the tensor assembly 400 (or generally between the sizer body 110B and the sizer frame 401), as shown on the angular scale 561 (see FIGS. 9 and 14). The angular scale 561 is calibrated to show the angle of relative rotation between the posterior feet 162 of the AP sizer body 110B and the posterior feet 410 of the tensor assembly 400. For example, if the actual rotation angle of the knob 560 is "x" and the relative rotation between the AP sizer body 110B and the tensor frame 401 is "y", then the rotation transmission ratio is "x" divided by "y". In the embodiment of the universal integrated instrument illustrated in FIGS. 9-17, a rotation transmission ratio is about 6.7. Generally, a rotation transmission ratio of about 5 to about 20 can be used. Accordingly, graduated and controlled balancing of the ligaments can be achieved. The resected femur can then be sized using the AP sizer assembly 102B as discussed above in connection with the unilateral integrated orthopedic instrument 100A.

Referring to FIGS. 18-22, another embodiment of the universal integrated orthopedic instrument 100C is illustrated. The universal integrated orthopedic instrument 100C includes an AP (anterior-posterior) sizer assembly 102C for sizing the femur, a tensor (or balancer) assembly 400C for tensioning the ligaments and balancing the knee and a rotation mechanism 600. The AP sizer assembly 102C is rotatably coupled to the tensor assembly 400C via the rotation mechanism 600. The AP sizer assembly 102C can also include a sizer body 110C, a sizer slider 120 and a sizer stylus 130. The sizer body 110C has a U-shaped upper portion 112 that includes two pads 142 and a lower portion 116C that is recessed from the upper portion 112 for receiving a flange 408 of a tensor frame 401 of the tensor assembly 400C. A rod 118 extends between the pads 142 and is spaced apart from the upper portion 112. Similarly, a base 146C extends from the lower portion 116C of the sizer body 110C. The base 146C defines a U-shaped recess 166 substantially parallel to the rod 118. A projection 190 of the sizer slider 120 is received in the recess 166 for sliding contact thereon. The sizer slider 120 also includes a through-hole 192 receiving the rod 118. The sizer slider 120 can slide along the rod 118 and along a track defined by the recess 166. This embodiment is similar to the universal integrated orthopedic instrument 100B, except for the rotation mechanism 600 which provides a direct rotation transmission. The rotation mechanism 600 includes a plate 650 attached to an AP sizer body 110C, a pivot bolt 620 along a pivot axis P and a set screw 630 for controlling the rotation (see FIGS. 18 and 22). The pivot bolt 620 can be rotated with a driver using driver formations 622, shown in FIG. 18. The pivot bolt 620 passes through a hole 163 of the AP sizer body 110C and a corresponding hole 405 of the tensor frame 401. A set screw 630 with driver formations 632 passes from the plate 650 through a threaded hole 167 of the AP sizer body 116C. The set screw 630 can be driven from the plate 650 using a driver to engage the driver formation 632 until the set screw 630 engages the tensor frame 401 and prevents further rotation (see FIG. 18).

As discussed above, the present teachings provide various embodiments of an integrated orthopedic instrument that can be used to replace separate AP sizer and tensor balancing instruments used in knee arthroplasty. Each integrated instrument of the present teachings is not merely an addition of separate instruments, but has components customized to one another to work synergistically and provide a single instrument for the surgeon. In this respect, an AP sizer assembly and a tensor assembly are customized to work as a single unit having a separate but corresponding pairs of posterior feet and a rotation mechanism integrally coupled to the AP sizer assembly and the tensor assembly such that one of the pairs of posterior feet can rotate relative to the other for ligament tensioning and knee balancing. In one embodiment, a unilateral integrated orthopedic instrument is provided, i.e., an integrated orthopedic instrument customized to be used with only one of a patient's two knees, such as a left knee, for example, and a similar mirror image for the opposite knee, i.e., the right knee. In another embodiment, a universal integrated orthopedic instrument is provided, i.e., an integrated orthopedic instrument customized to be used for both a left knee and a right knee. Two examples of universal integrated orthopedic instruments are provided having different rotation mechanisms and different types of rotation control, including rotation transmission control.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An orthopedic instrument for knee arthroplasty comprising:
    an anterior-posterior sizer assembly having a stylus, a sizer body including medial and lateral posterior feet extending substantially perpendicularly from the sizer body, and a sizer slider slidable relative to the sizer body along a medial-lateral direction relative to a patient's knee, the sizer body having a channel therethrough;
    a tensor assembly including a tensor frame having a central portion, medial and lateral wings extending at an angle from the central portion, a tab extending from the central portion between the medial and lateral wings and having an elongated aperture, and medial and lateral posterior feet extending substantially perpendicularly to the central portion;
    a knob rotatably coupled to the tensor assembly, the knob having a cam groove on a side facing the sizer body; and
    a cam slider slidably supported in the channel of the sizer body in a medial-lateral direction, the cam slider including a first post guidable by the cam groove of the knob and a second post movably received in the elongated aperture of the tensor frame, such that rotating the knob rotates the sizer body relative to the tensor frame and changes a relative gap between the corresponding posterior feet of the sizer body and the tensor frame.

2. The orthopedic instrument of claim 1, further comprising a plate having an angular scale on a first side and a recess on a second side opposite the first side and facing the sizer body, wherein the knob is rotatably received in the recess of the plate.

3. The orthopedic instrument of claim 2, wherein the plate supports a pivot bolt, the pivot bolt passing through the sizer body and through the central portion of the tensor frame of the sizer assembly, the pivot bolt configured to rotate the sizer body relative to the tensor frame.

4. The orthopedic instrument of claim 1, further comprising a spring having a finger movably engaging a fluted peripheral wall portion of the knob.

5. The orthopedic instrument of claim 1, further comprising at least one rod supported on the channel of the sizer body and passing through the cam slider.

6. The orthopedic instrument of claim 1, wherein the sizer body includes a recess receiving the tab of the tensor frame.

7. The orthopedic instrument of claim 1, wherein the lateral posterior feet of the tensor assembly have a thickness that is the same as a thickness of the medial posterior feet of the tensor assembly such that equal gaps are formed between the corresponding medial posterior feet and the sizer body and between the corresponding lateral posterior feet and the sizer body.

8. The orthopedic instrument of claim 1, further comprising an angular scale formed on the knob.

9. An orthopedic instrument for knee arthroplasty comprising:
   an anterior-posterior sizer assembly having a stylus, a sizer body including medial and lateral posterior feet extending substantially perpendicularly from the sizer body, and a sizer slider slidable relative to the sizer body along a medial-lateral direction relative to a patient's knee, the sizer body having a channel therethrough;
   a tensor assembly including a tensor frame having a central portion, medial and lateral wings extending at an angle from the central portion, a tab extending from the central portion between the medial and lateral wings and having an elongated aperture, and medial and lateral posterior feet extending substantially perpendicularly to the central portion;
   a plate having an angular scale on a first side and a recess on a second side opposite the first side and facing the sizer body;
   a knob rotatably received in the recess of the plate, the knob having a cam groove on a side facing the sizer body; and
   a cam slider slidably supported in the channel of the sizer body in a medial-lateral direction, the cam slider including a first post guidable by the cam groove of the knob and a second post movably received in the elongated aperture of the tensor frame, such that rotating the knob rotates the sizer body relative to the tensor frame and changes a relative gap between the corresponding posterior feet of the sizer body and the tensor frame.

10. The orthopedic instrument of claim 9, further comprising a spring having a finger movably engaging a fluted peripheral wall portion of the knob.

11. The orthopedic instrument of claim 9, further comprising at least one rod supported on the channel of the sizer body and passing through the cam slider.

12. The orthopedic instrument of claim 9, wherein the sizer body includes a recess receiving the tab of the tensor frame.

13. The orthopedic instrument of claim 9, wherein the lateral posterior feet of the tensor assembly have a thickness that is the same as a thickness of the medial posterior feet of the tensor assembly such that equal gaps are formed between the corresponding medial posterior feet and the sizer body and between the corresponding lateral posterior feet and the sizer body.

14. The orthopedic instrument of claim 9, further comprising an angular scale formed on the knob.

15. The orthopedic instrument of claim 9, wherein the plate supports a pivot bolt, the pivot bolt passing through the sizer body and through the central portion of the tensor frame of the sizer assembly, the pivot bolt configured to rotate the sizer body relative to the tensor frame.

16. The orthopedic assembly of claim 9, wherein the tensor assembly is configured for ligament balancing of both a right knee and a left knee.

* * * * *